(12) United States Patent
Iwata et al.

(10) Patent No.: US 11,918,327 B2
(45) Date of Patent: Mar. 5, 2024

(54) SPHYGMOMANOMETER, BLOOD PRESSURE MEASUREMENT METHOD, AND DEVICE

(71) Applicants: OMRON CORPORATION, Kyoto (JP); OMRON HEALTHCARE CO., LTD., Muko (JP)

(72) Inventors: Shohei Iwata, Kyoto (JP); Takanori Nishioka, Kyoto (JP); Akira Tampo, Kyoto (JP); Yoshihiko Sano, Kyoto (JP); Takeshi Kubo, Kyoto (JP); Yu Higashimura, Kyoto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 719 days.

(21) Appl. No.: 16/439,761

(22) Filed: Jun. 13, 2019

(65) Prior Publication Data

US 2019/0290143 A1 Sep. 26, 2019

Related U.S. Application Data

(63) Continuation of application No. PCT/JP2017/042084, filed on Nov. 22, 2017.

(30) Foreign Application Priority Data

Dec. 28, 2016 (JP) ................................. 2016-255838

(51) Int. Cl.
*A61B 5/022* (2006.01)
*A61B 5/00* (2006.01)

(52) U.S. Cl.
CPC .......... *A61B 5/02241* (2013.01); *A61B 5/022* (2013.01); *A61B 5/681* (2013.01); *A61B 2562/0247* (2013.01)

(58) Field of Classification Search
None
See application file for complete search history.

(56) References Cited

U.S. PATENT DOCUMENTS 5,620,001 A * 4/1997 Byrd .................. A61B 5/02233
600/490
5,904,145 A * 5/1999 Reid ..................... A61F 13/069
606/202

(Continued)

FOREIGN PATENT DOCUMENTS

CN 1517061 A 8/2004
CN 1748637 A 3/2006

(Continued)

OTHER PUBLICATIONS

Machine Translation of JP-2005334124-A. Retrieved from EPO. (Year: 2021).*

(Continued)

*Primary Examiner* — Benjamin S Melhus
*Assistant Examiner* — Samuel C Kim
(74) *Attorney, Agent, or Firm* — Oliff PLC

(57) ABSTRACT

A sphygmomanometer according to the present disclosure includes a main body that is mounted with a pump and is to be disposed on a dorsal surface of a wrist and a cuff that is to be attached around the wrist. The cuff extends along a circumferential direction of the wrist from an ulnar side end portion of the main body to a palmar surface and is set to a length covering an ulnar artery or a length covering a radial artery beyond the ulnar artery of a wrist having a preset maximum wrist circumference. A fluid is supplied from the pump to the cuff to press the wrist. A blood pressure is calculated based on a pressure of the fluid contained in the cuff.

15 Claims, 26 Drawing Sheets

(56) References Cited

U.S. PATENT DOCUMENTS

| | | |
|---|---|---|
| 6,336,901 B1 | 1/2002 | Itonaga et al. |
| 2002/0170359 A1 | 11/2002 | Yamakoshi et al. |
| 2006/0178584 A1 | 8/2006 | Karo et al. |
| 2009/0234381 A1* | 9/2009 | Karo ................ A61B 5/742 606/202 |
| 2010/0234743 A1* | 9/2010 | Kohyama .......... A61B 5/02233 600/499 |
| 2011/0112412 A1* | 5/2011 | Sano ................. A61B 5/02233 600/499 |

FOREIGN PATENT DOCUMENTS

| | | | | |
|---|---|---|---|---|
| CN | 105686817 A | * | 6/2016 | |
| JP | H03-60356 U | | 6/1991 | |
| JP | H06-11701 U | | 2/1994 | |
| JP | H11-309119 A | | 11/1999 | |
| JP | 2002-102182 A | | 4/2002 | |
| JP | 2003-24286 A | | 1/2003 | |
| JP | 2005334124 A | * | 12/2005 | |
| JP | 2006-212282 A | | 8/2006 | |
| JP | 2010-119447 A | | 6/2010 | |
| JP | 2011-212159 A | | 10/2011 | |

OTHER PUBLICATIONS

Machine Translation of CN 105686817 A . Retrieved from translationportal.epo.org on Sep. 20, 2022. (Year: 2022).*
Jan. 9, 2019 International Search Report issued in Japanese Patent Application No. PCT/JP2017/042084.
Jun. 9, 2021 Office Action issued in Chinese Patent Application No. 201780074111.9.

* cited by examiner

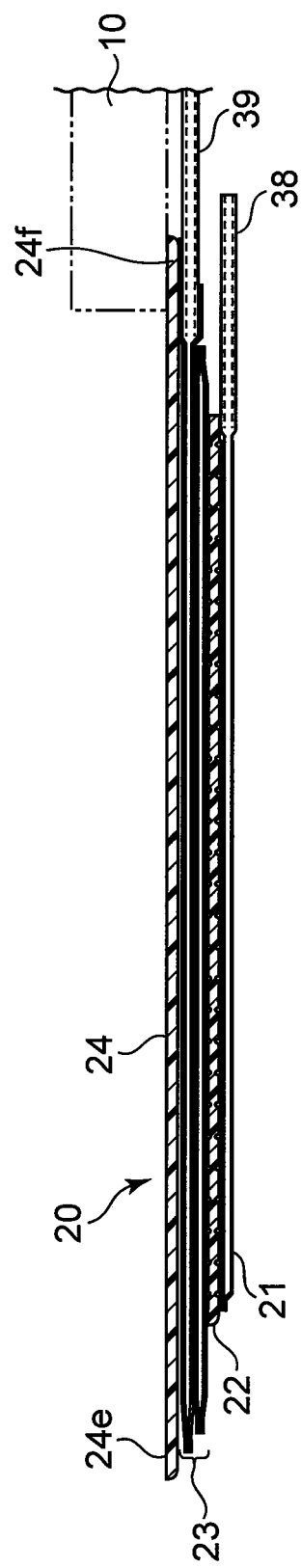

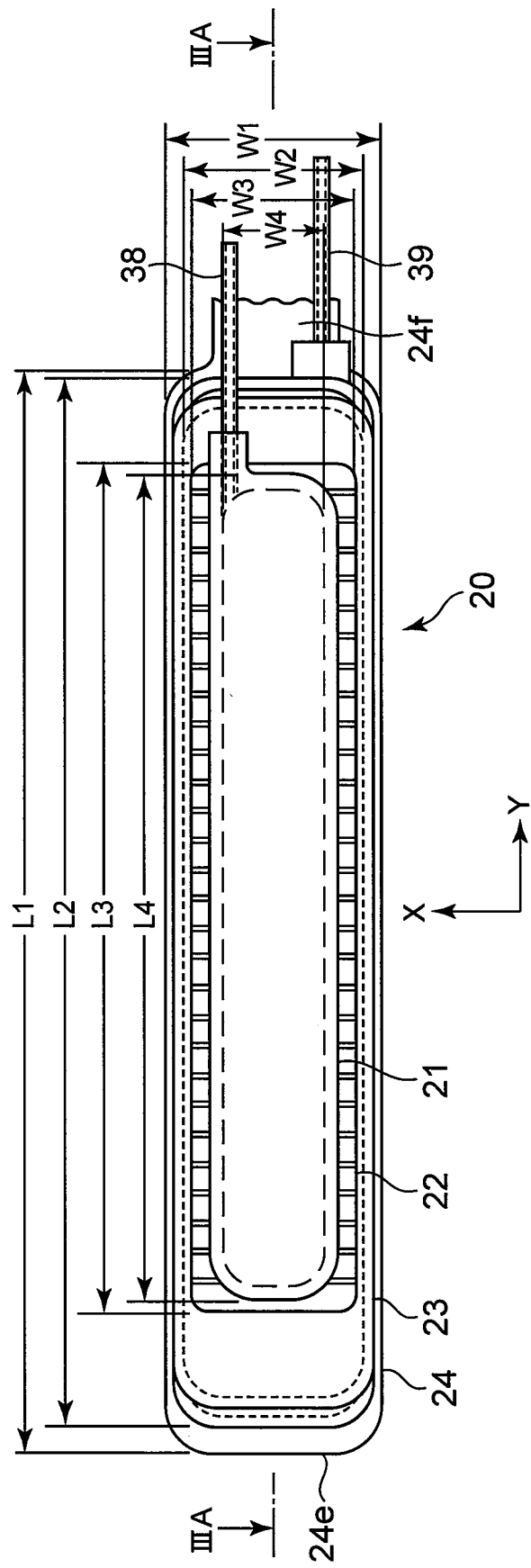

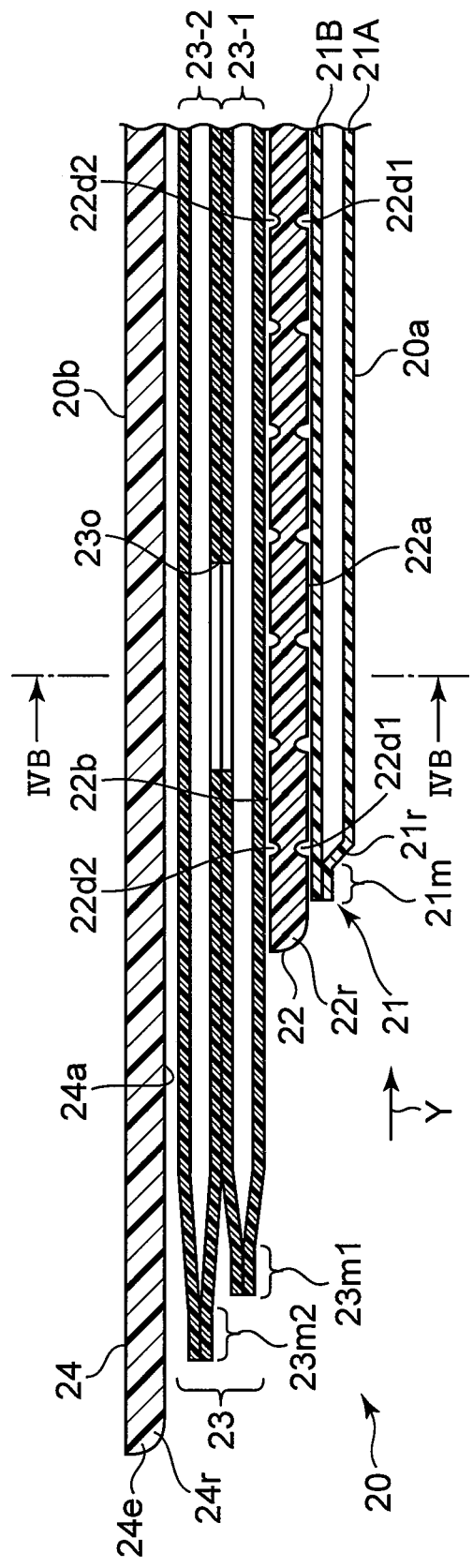

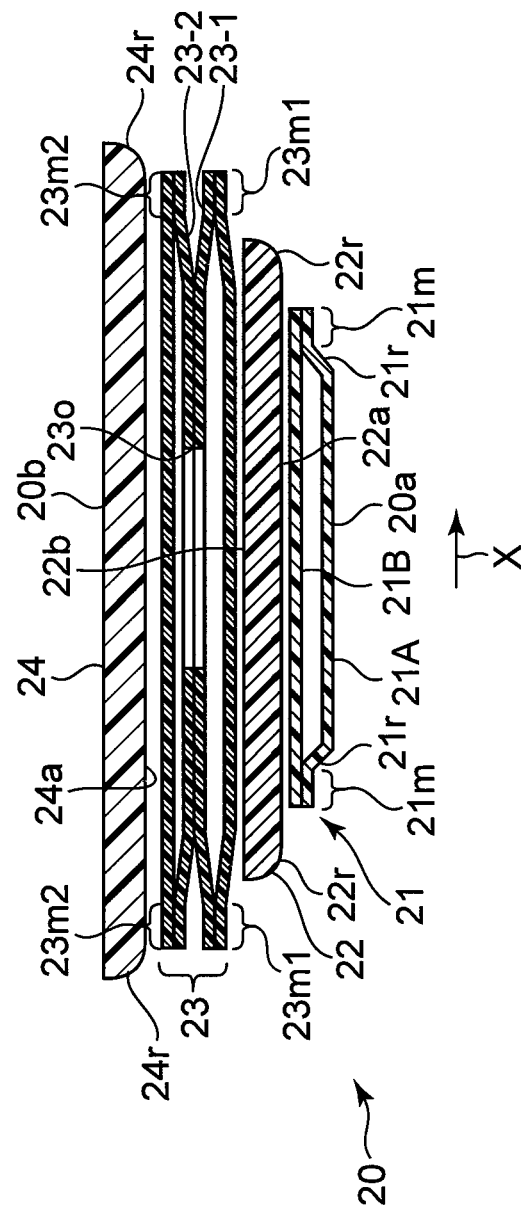

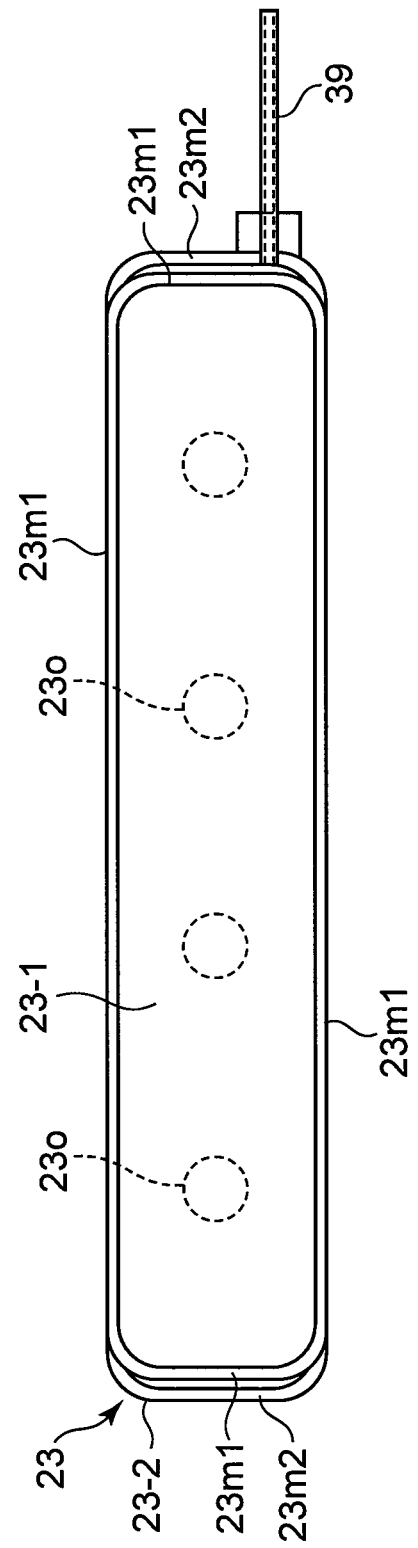

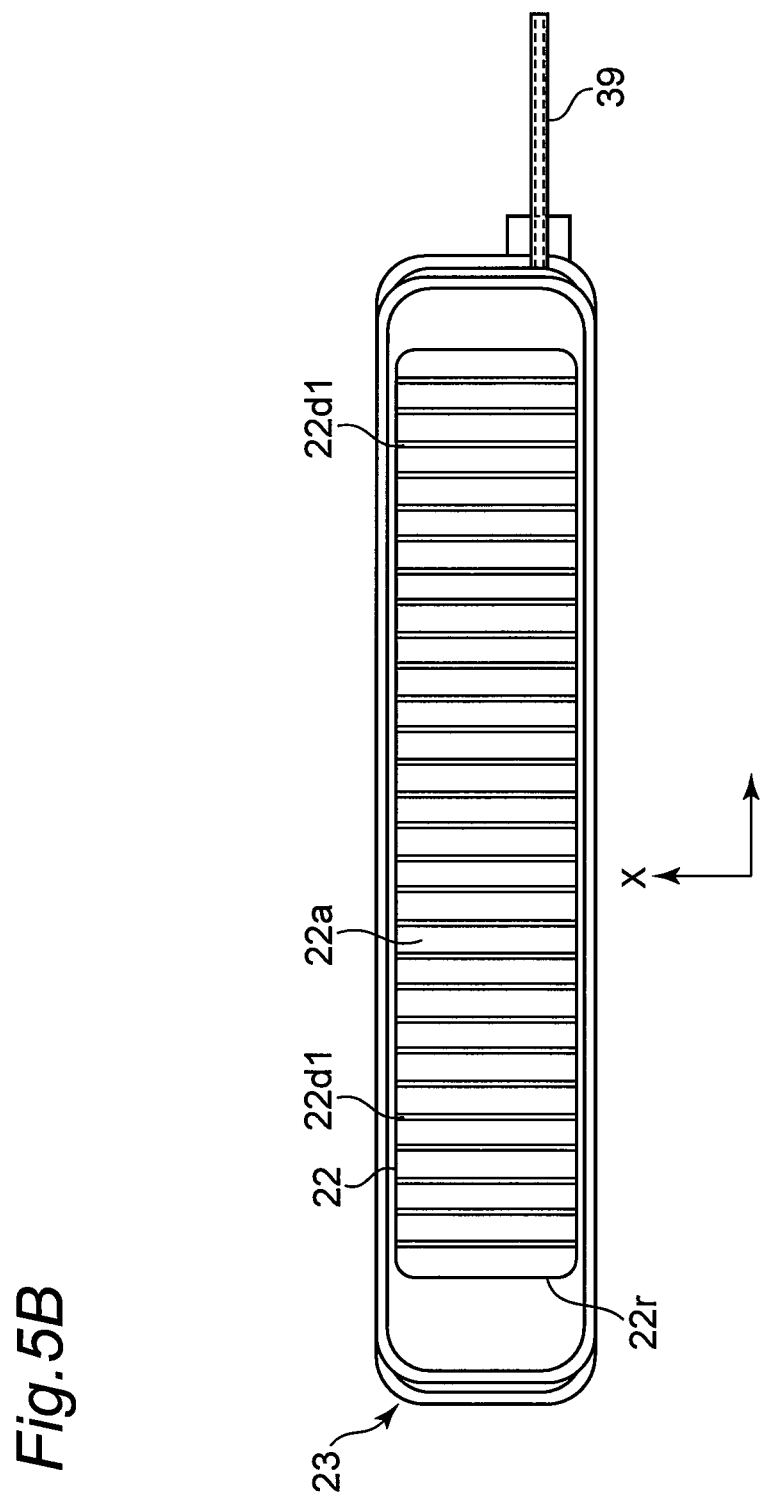

SPHYGMOMANOMETER, BLOOD PRESSURE MEASUREMENT METHOD, AND DEVICE

CROSS-REFERENCE TO RELATED APPLICATION

This is a continuation application of International Application No. PCT/JP2017/042084, with an International filing date of Nov. 22, 2017, which claims priority of Japanese Patent Application No. 2016-255838 filed on Dec. 28, 2016, the entire content of which is hereby incorporated by reference.

TECHNICAL FIELD

The present invention relates to a sphygmomanometer, and more particularly, a wrist-type sphygmomanometer that includes a main body that is to be disposed on a dorsal surface (surface corresponding to a back side of a hand) of an outer circumferential surface of a wrist as a measurement target site and a cuff that extends from the main body and to be mounted around the wrist. The present invention also relates to a blood pressure measurement method for measuring a blood pressure at a measurement target site. Furthermore, the present invention relates to a device including a blood pressure measurement function.

BACKGROUND ART

Conventionally, as this type of sphygmomanometer, for example, as disclosed in Patent Literature 1 (JP H6-11701 U), there is known a wristwatch blood pressure meter in which a blood pressure measurement device is miniaturized and incorporated into a wristwatch so that it is constantly attached to an arm. In the wristwatch blood pressure meter, armbands extend from a main body (case body) on which a pump is mounted to both sides along a circumferential direction of the wrist. A cuff (air bag) is provided on an inner circumferential surface of each of the armbands on both sides thereof. When being attached to the wrist, the tips of the armbands are fastened with Velcro. At the time of blood pressure measurement, air is supplied and pressurized from the pump to the cuff (air bag) provided on the inner circumferential surface of the armbands on both sides. Then, the pulsation of a blood vessel is detected by a pressure sensor as a pressure of the cuff, and thus a blood pressure value is obtained.

SUMMARY OF INVENTION

However, in the sphygmomanometer described above, if the main body (case body) is disposed on the dorsal surface of the wrist, a fastening point (Velcro) of the tips of the armbands is disposed on the palmar surface (surface corresponding to a palm side of the hand) of the wrist. If the fastening point (Velcro) of the tips of the armbands is disposed facing an artery passing portion of the wrist, it becomes difficult to detect the pulsation of the artery as a pressure of the cuff, and the blood pressure measurement accuracy is impaired.

Here, given that the cuff extends from one end of the main body to only one side along the circumferential direction of the wrist, the palmar surface of the wrist can be covered by the cuff, and hence the pulsation of the artery can be detected as a pressure of the cuff, and the blood pressure measurement accuracy can be enhanced. However, depending on the cuff length setting, there is a problem that the length of the cuff is insufficient when the user with a large wrist circumference uses the sphygmomanometer, and that when the user with a small wrist circumference uses the sphygmomanometer, a portion continuing to the tip end of the cuff becomes surplus making difficult to be attached.

Therefore, an object of the present invention is to provide a wrist-type sphygmomanometer and a device that include a main body that is to be disposed on a dorsal surface of an outer circumferential surface of a wrist as a measurement target site and a cuff that extends from one end of the main body and to be mounted around the wrist, the wrist-type sphygmomanometer and the device being preferably applicable to users (subjects) with wrist circumferences of various sizes. Another object of the present invention is to provide a blood pressure measurement method for measuring a blood pressure of a wrist as a measurement target site with such a main body and a cuff, the blood pressure measurement method being preferably applicable to users with wrist circumferences of various sizes.

The inventor has focused on the fact that, in the cross section of the wrist (a left wrist 90 in this example) schematically shown in FIG. 19, there is a magnitude relationship $\Delta\theta > \Delta\theta'$ with respect to the angles $\Delta\theta$ and $\Delta\theta'$ when a radial artery 91 and an ulnar artery 92 are viewed respectively from a center 90c of the wrist, with a boundary surface 90h between a dorsal surface 90g and a palmar surface 90p as a reference. According to the magnitude relationship, a counterclockwise (in FIG. 19) angle $\theta 1$ from the center 90s of the dorsal surface 90g to the radial artery 91 is smaller than a clockwise (in FIG. 19) angle $\theta 2$ from the center 90s of the dorsal surface 90g to the ulnar artery 92. This means that the length of the cuff can be set shorter when covering the radial artery 91 beyond the ulnar artery 92 with the cuff extending counterclockwise (in FIG. 19) along the circumferential direction of the wrist from an ulnar side end portion (end portion on a side close to an ulna 94) of the main body (disposed on the dorsal surface 90g) as compared to when covering the ulnar artery 92 beyond the radial artery 91 with the cuff extending clockwise (in FIG. 19) along the circumferential direction of the wrist from a radial side end portion (end portion on a side close to a radius 93) of the main body, conversely. The present invention has been made based on this finding.

In order to solve the problem described above, a sphygmomanometer of the present disclosure comprises:
  a main body that is mounted with a pump and is to be disposed on a dorsal surface of a wrist as a measurement target site; and
  a cuff that extends along a circumferential direction of the wrist from an ulnar side end portion of the main body to a palmar surface and is to be attached around the wrist,
  wherein the cuff includes
  a belt that extends from the main body and is to be attached around the wrist, and
  a cuff structure that has a band shape and a set length, and that is disposed facing an inner circumferential surface of the belt and has one end attached to an ulnar side end portion of the main body,
  the sphygmomanometer includes
  a pressurization control unit that performs control of supplying a fluid from the pump to the cuff structure to press the wrist, and
  a blood pressure calculation unit that calculates a blood pressure based on a pressure of a fluid contained in the cuff structure; and when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference.

In the present specification, the "dorsal surface" of the wrist refers to a semi-circumferential surface corresponding to the back side of the hand of the outer circumferential surface of the wrist. The "palmar surface" of the wrist refers to a semi-circumferential surface corresponding to the palm side of the hand of the outer circumferential surface of the wrist. The "boundary line on a radial side" refers to a boundary line close to the radius, of the two boundary lines between the dorsal surface and the palmar surface.

The "ulnar side end portion" of the main body refers to an end portion of the main body disposed on a side close to the ulna in the circumferential direction of the wrist. On the other hand, the "radial side end portion" of the main body refers to an end portion of the main body disposed on a side close to the radius in the circumferential direction of the wrist.

Also, the "preset maximum wrist circumference" refers to a length set as the maximum wrist circumference that can be measured by the sphygmomanometer in product specifications of the sphygmomanometer, for example, 215 mm.

Also, when simply referred to as the "wrist", it is a generic term for wrists having various sizes of wrist circumferences.

As for the "belt" that "extends from the main body" in the present specification, the main body and the belt may be integrally molded, or the main body and the belt may be formed separately from each other and the belt may be attached to the main body. Furthermore, as for the belt itself, a first belt portion that extends in one direction from the main body and a second belt portion that extends in the other direction from the main body may be fastened or released by a clasp, or may be coupled by an openable buckle. The "inner circumferential surface" of the belt refers to a surface that is on the inner circumferential side with the belt being attached around the measurement target site. Similarly, the "inner circumferential surface" of the pressure cuff refers to a surface that is on the inner circumferential side with the pressure cuff being attached around the measurement target site.

In another aspect, a blood pressure measurement method of the present disclosure is a method for measuring a blood pressure of a wrist using a sphygmomanometer, the sphygmomanometer including:
 a main body that is mounted with a pump and is to be disposed on a dorsal surface of a wrist as a measurement target site, and
 a cuff that extends along a circumferential direction of the wrist from an ulnar side end portion of the main body to a palmar surface and is to be attached around the wrist,
 wherein the cuff includes
 a belt that extends from the main body and is to be attached around the wrist, and
 a cuff structure that has a band shape and a set length, and that is disposed facing an inner circumferential surface of the belt and has one end attached to an ulnar side end portion of the main body, and
 when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference, and
the blood pressure measurement method comprises:
 performing control of supplying a fluid from the pump to the cuff structure to press the wrist; and
 calculating a blood pressure based on a pressure of a fluid contained in the cuff structure.

In another aspect, a device of the present disclosure is a device comprising a main body that is mounted with blood pressure measurement elements and is to be disposed on a dorsal surface of a wrist as a measurement target site,
 wherein the blood pressure measurement elements include
 a pump mounted to the main body, and
 a cuff that extends along a circumferential direction of the wrist from an ulnar side end portion of the main body to a palmar surface and is to be attached around the wrist,
 wherein the cuff includes
 a belt that extends from the main body and is to be attached around the wrist, and
 a cuff structure that has a band shape and a set length, and that is disposed facing an inner circumferential surface of the belt and has one end attached to an ulnar side end portion of the main body,
 the device includes
 a pressurization control unit that performs control of supplying a fluid from the pump to the cuff structure to press the wrist, and
 a blood pressure calculation unit that calculates a blood pressure based on a pressure of a fluid contained in the cuff structure; and
 when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference.

The "device" of the present disclosure widely includes a device having a blood pressure measurement function, and may be configured as, for example, a wristwatch-type wearable device such as a smart watch.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 3B shows a planar layout when a cuff structure in FIG. 2 is unfolded with its inner circumferential surface at the forefront. FIG. 3A shows a cross section taken along line IIIA-IIIA in FIG. 3B.

FIG. 4A is an enlarged view showing a vicinity of a tip end portion of a cuff structure in FIG. 3B. FIG. 4B shows a cross section taken along line IVB-IVB in FIG. 4A.

FIG. 5A shows a planar layout of a pressure cuff included in the cuff structure.

FIG. 5B shows a planar layout of a back plate included in the cuff structure, with the pressure cuff as a background.

DESCRIPTION OF EMBODIMENTS

Hereinafter, embodiments of the present invention will be described in detail with reference to the drawings.

(Configuration of Sphygmomanometer)

Figure 1:
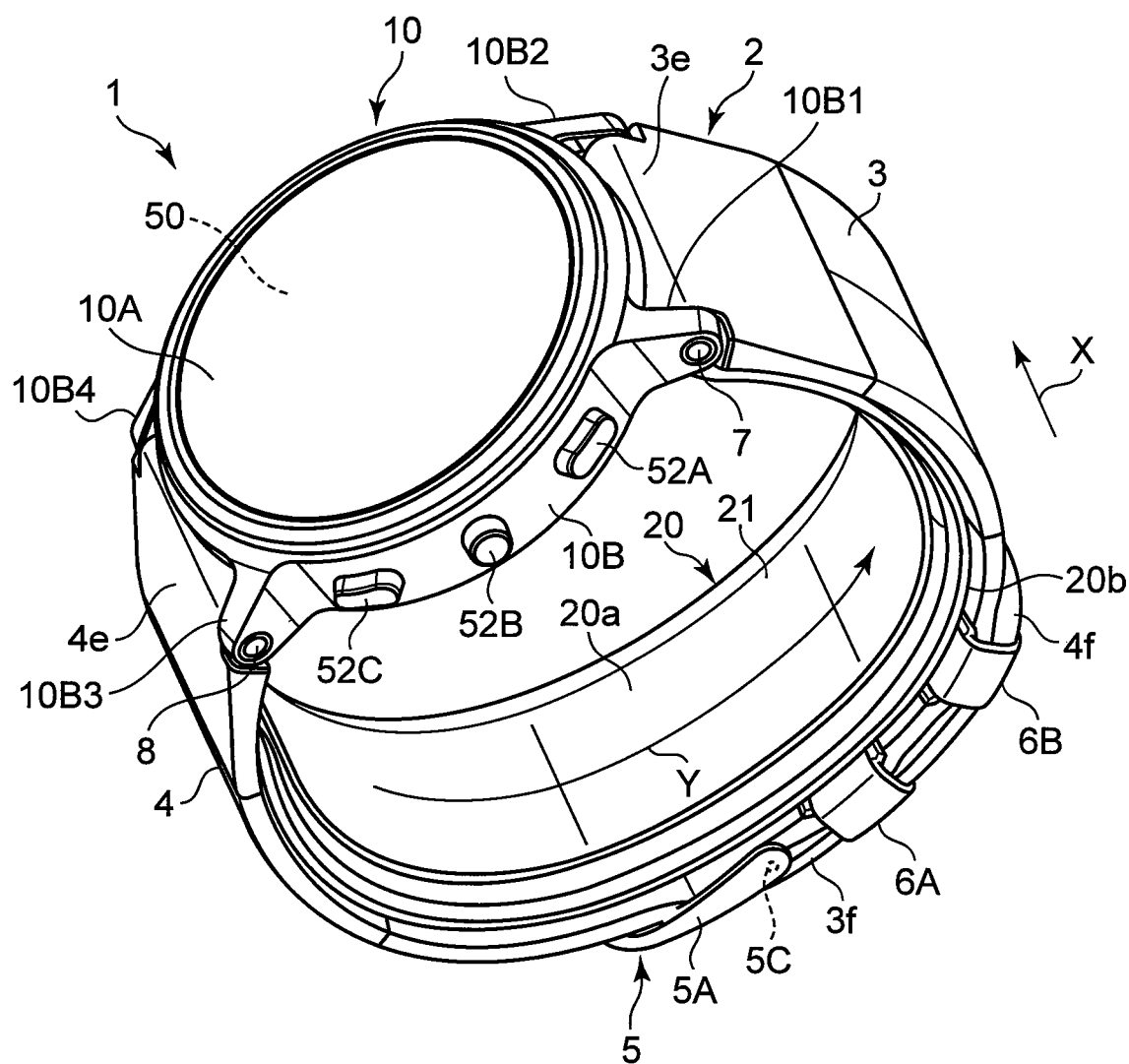
FIG. 1 shows an appearance of a sphygmomanometer according to an embodiment of the present invention as viewed obliquely, with a belt fastened.
Figure 2:
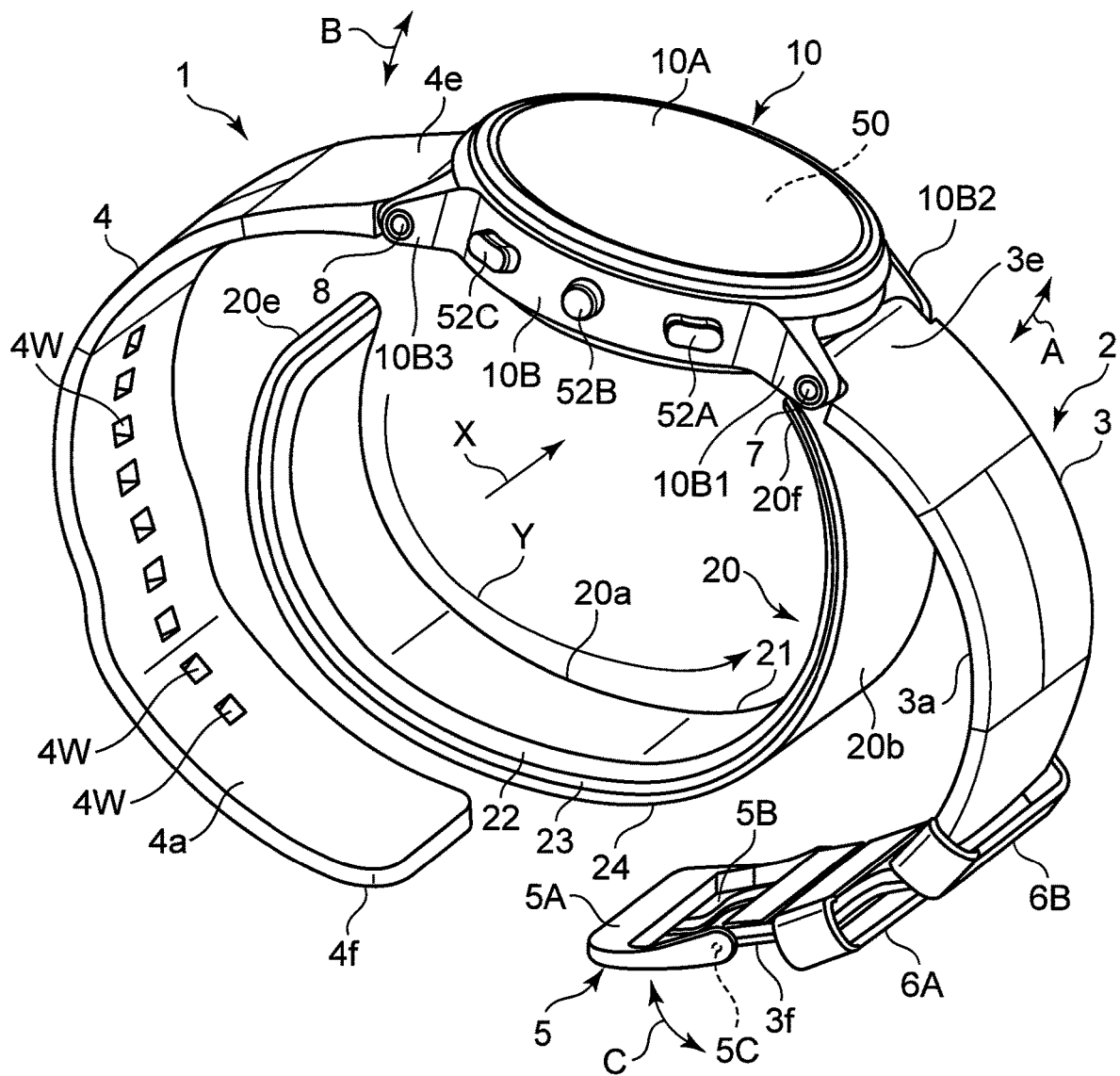
FIG. 2 shows an appearance of the sphygmomanometer as viewed obliquely, with a belt released.

FIG. 1 shows an appearance of a sphygmomanometer according to an embodiment of the present invention (indicated by a reference numeral 1 as a whole) as viewed obliquely, with a belt 2 fastened. FIG. 2 shows the appearance of the sphygmomanometer 1 as viewed obliquely, with the belt 2 released.

Figure 13A:
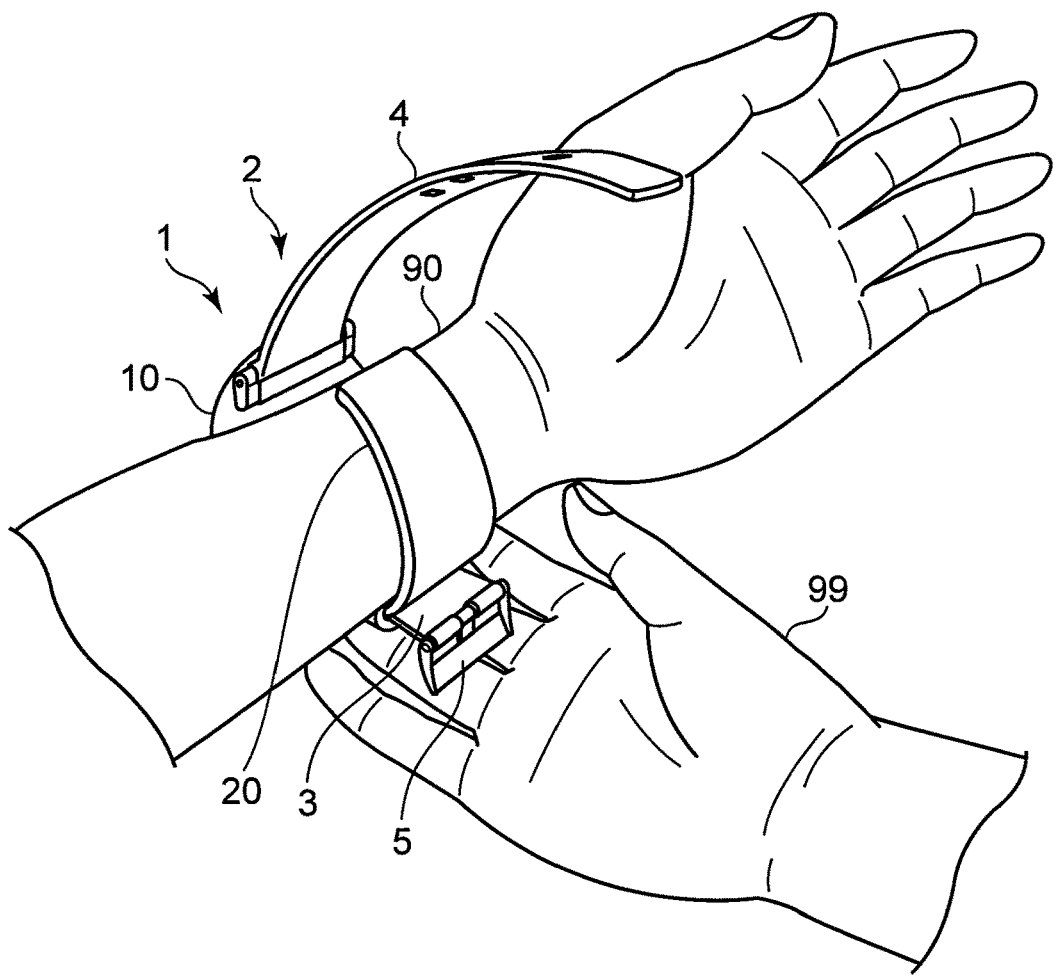
FIG. 13A is a perspective view showing a manner in which a user attaches a cuff structure to the left wrist using the right hand.
Figure 13B:
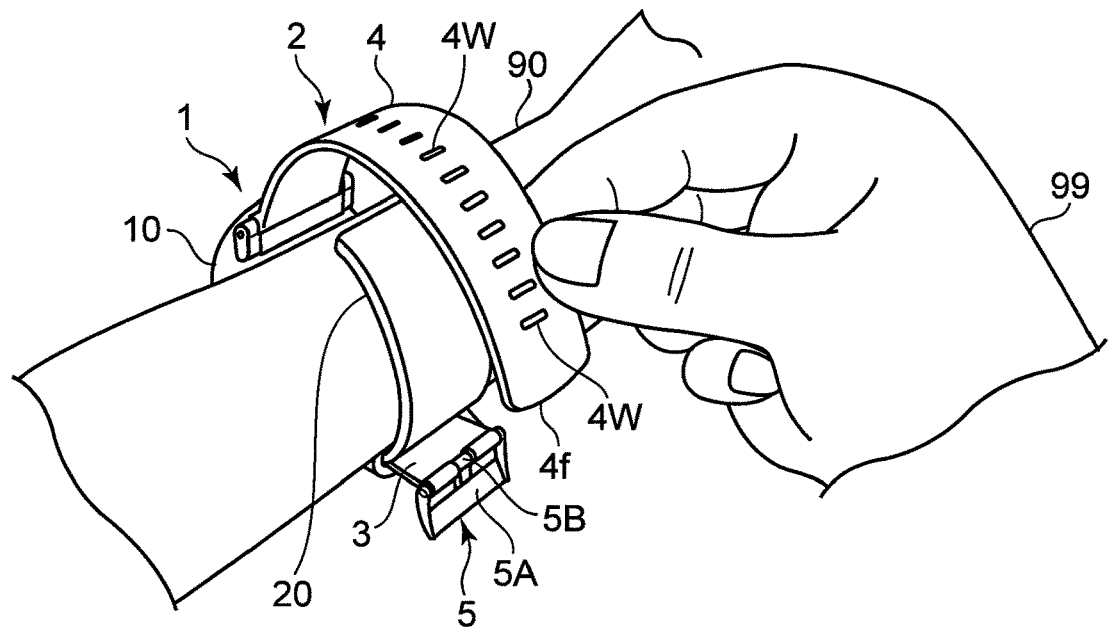
FIG. 13B is a perspective view showing a manner in which a user collectively surrounds the left wrist and the cuff structure with a belt using the right hand.
Figure 13C:
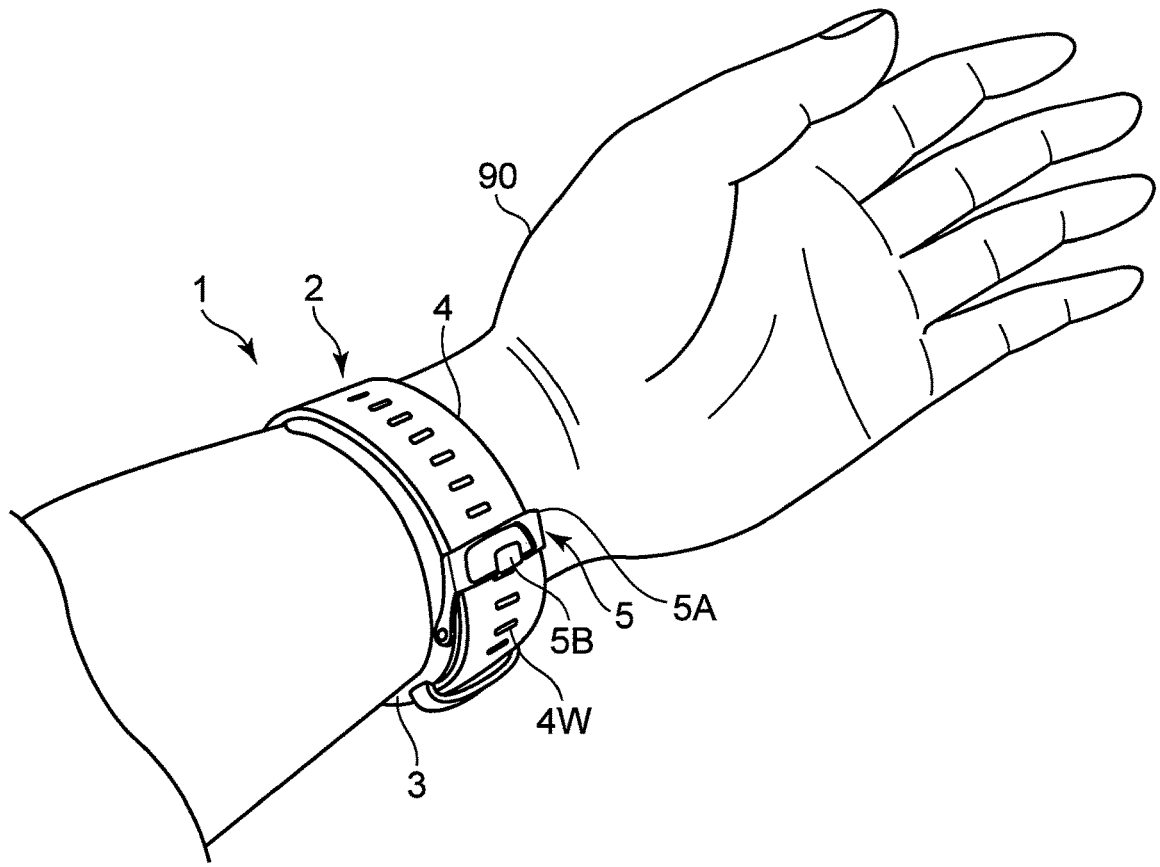
FIG. 13C is a perspective view showing a manner in which the sphygmomanometer is attached to the user's left wrist.

As shown in these figures, the sphygmomanometer 1 roughly includes a main body 10, the belt 2 which extends from the main body 10 and is to be attached around a measurement target site (in this example, as shown in FIG. 13C described later, a left wrist 90 is assumed to be the measurement target site), and a cuff structure 20 that has a band shape and has one end 20f attached to the main body 10. The dimension of the belt 2 in a width direction X is set to 29 mm in this example. The thickness of the belt 2 is set to 2 mm in this example.

In this example, the main body 10 has a substantially short cylindrical case 10B, a circular glass 10A attached to an upper portion (in FIGS. 1 and 2) of the case 10B, and a back lid 10C (see FIG. 6) attached to a lower portion of the case 10B. Side surfaces of the case 10B are provided with left and right (in FIGS. 1 and 2) pairs of protruding lugs 10B1 and 10B2 and 10B3 and 10B4 for attaching the belt 2, respectively, in an integral manner.

In a glass 10A of the upper portion of the case 10B, an indicator 50 serving as a display screen is provided. The side surface of the front side (in FIGS. 1 and 2) of the main body 10 is provided with a measurement switch 52A for instructing start or stop of blood pressure measurement, a home switch 52B for causing a display screen of the indicator 50 to return to a predetermined home screen, and a recording call switch 52C for performing an instruction of causing the indicator 50 to display measurement records such as past blood pressure and activity amount (these switches are collectively referred to as an operation unit 52). Blood pressure measurement elements including a pump 30 (to be described in detail later) are mounted to the inside of the main body 10. In this example, the sphygmomanometer 1 includes functions of an activity amount meter and a pulsimeter. That is, the sphygmomanometer 1 is configured as a multifunctional device having an aspect of a wristwatch-type wearable device. The main body 10 is formed to be small and thin so as not to interfere with the daily activities of the user.

As can be clearly seen from FIG. 2, the belt 2 includes a band-shaped first belt portion 3 which extends from the main body 10 to one side (right side in FIG. 2) in one direction, and a band-shaped second belt portion 4 which extends from the main body 10 to the other side (left side in FIG. 2) in the one direction. A basal portion 3e of the first belt portion 3 on a side closer to the main body 10 is attached rotatably to the lugs 10B1 and 10B2 of the main body 10 via a coupling rod 7 (publicly known spring rod) that extends in the width direction X of the belt, as shown by a double arrow A. Similarly, a basal portion 4e of the second belt portion 4 on a side closer to the main body 10 is attached rotatably to the lugs 10B3 and 10B4 of the main body 10 via a coupling rod 8 (publicly known spring rod) that extends in the width direction X of the belt, as shown by a double arrow B.

A clasp 5 is attached to a tip end portion 3f of the first belt portion 3 on the side far from the main body 10. The clasp 5 is of a publicly known type and includes a substantially U-shaped frame 5A, a prong 5B, and a coupling rod 5C that extends in the width direction X of the belt. The frame 5A and the prong 5B are each rotatably attached to the tip end portion 3f of the first belt portion 3 on the side far from the main body 10 as indicated by a double arrow C via the coupling rod 5C. Ring-shaped belt holding portions 6A and 6B are integrally provided between the tip end portion 3f and the basal portion 3e of the first belt portion 3 at a predetermined position in the longitudinal direction of the first belt portion 3 (corresponding to a circumferential direction Y of the left wrist 90). An inner circumferential surface 3a of the first belt portion 3 does not protrude to the inner circumferential side at the locations of the belt holding portions 6A and 6B, and is formed to be generally flat (locally, although curved as a whole). Thus, the belt 2 uniformly surrounds and restrains the outer circumferential side of the cuff structure 20.

A plurality of small holes 4w, 4w, . . . are formed in the second belt portion 4 between the basal portion 4e and a tip end portion 4f on the side far from the main body 10 so as to penetrate the second belt portion 4 in the thickness direction. When the first belt portion 3 and the second belt portion 4 are fastened, a portion continuing to the tip end portion 4f of the second belt portion 4 is passed through the frame 5A of the clasp 5, and the prong 5B of the clasp 5 is inserted into any one of the plurality of small holes 4w, 4w, . . . of the second belt portion 4. Due to this, as shown in FIG. 1, the first belt portion 3 and the second belt portion 4 are fastened.

In this example, the first belt portion 3 and the second belt portion 4 constituting the belt 2 are made of a plastic material that has flexibility in the thickness direction and exhibits substantially no stretchability in the longitudinal direction (corresponding to the circumferential direction Y of the left wrist 90). This allows the belt 2 to be easily wrapped around and restrain the outer circumferential side of the cuff structure 20 at the time of attachment, and to help to press the left wrist 90 at the time of blood pressure measurement to be described later. The first belt portion 3 and the second belt portion 4 may be made of a leather material. While the frame 5A and the prong 5B that constitute the clasp 5 are made of a metal material in this example, the frame 5A and the prong 5B may be made of a plastic material.

As shown in FIG. 2, the cuff structure 20 includes a curler 24 disposed at the outermost circumference, a pressure cuff 23 disposed along the inner circumferential surface of the curler 24, a back plate 22 as a reinforcing plate disposed along the inner circumferential surface of the pressure cuff 23, and a sensing cuff 21 disposed along the inner circumferential surface of the back plate 22.

FIG. 3B shows a planar layout when the cuff structure 20 in FIG. 2 is unfolded with its inner circumferential surface 20a at the forefront. FIG. 3A shows a cross section taken along line IIIA-IIIA in FIG. 3B. FIG. 4A is an enlarged view showing a vicinity of a tip end portion of the cuff structure 20 in FIG. 3B. FIG. 4B shows a cross section taken along line IVB-IVB in FIG. 4A. FIG. 5A shows a planar layout of the pressure cuff 23. FIG. 5B shows a planar layout of the back plate 22, with the pressure cuff 23 as a background.

As shown in FIGS. 3A and 3B, the curler 24, the pressure cuff 23, the back plate 22, and the sensing cuff 21 each have a band shape elongated in one direction (Y direction). In this example, the dimension of the curler 24 in the width direction X is set to W1=28 mm, the dimension of the pressure cuff 23 (excluding the edge portions on both sides welded) in the width direction X is set to W2=25 mm, the dimension of the back plate 22 in the width direction X is set to W3=23 mm, and the dimension of the sensing cuff 21 in the width direction X (excluding the edge portions on both sides welded) is set to W4=15 mm. Also, the dimension of the curler 24 in a longitudinal direction Y (excluding a basal portion 24f attached to the main body 10) is set to L1=148 mm, the dimension of the pressure cuff 23 in the longitudinal direction Y is set to L2=140 mm, the dimension of the back plate 22 in the longitudinal direction Y is set to L3=114 mm, and the dimension of the sensing cuff 21 in the longitudinal direction Y is set to L4=110 mm. How to set the length of the cuff structure 20, in particular, the lengths of the pressure cuff 23 and the sensing cuff 21 will be described later.

As can be seen from FIGS. 4A and 4B, the sensing cuff 21 includes a first sheet 21A on the side in contact with the left wrist 90 and a second sheet 21B facing the first sheet 21A, and circumferential portions 21m of the first and second sheets 21A and 21B are in close contact with each other by welding to form a bag shape. In this example, as shown in FIG. 4B, slacks 21r and 21r that extend along the longitudinal direction Y of the sensing cuff 21 in a natural state are provided at a location continuing to the edge portions 21m and 21m on both sides of the sensing cuff 21 in the width direction X. As shown in FIG. 4A, the slack 21r that extends along the width direction X of the sensing cuff 21 in a natural state is provided at a location continuing to the edge portion 21m (only the tip end side is shown in FIG. 4A on both sides of the sensing cuff 21 in the longitudinal direction Y of the first sheet 21A. Such a slack 21r can be formed by a publicly known method, for example, when the circumferential portions 21m of the first and second sheets 21A and 21B are welded together so as to be brought into close contact. As can be seen from FIGS. 3A and 3B, an end portion on the basal side (+Y side) of the sensing cuff 21 in the longitudinal direction Y is attached with a flexible tube 38 for supplying a pressure transmission fluid (air in this example) to the sensing cuff 21 or discharging a pressure transmission fluid from the sensing cuff 21. The material of the first and second sheets 21A and 21B is made of a stretchable polyurethane sheet (thickness t=0.15 mm) in this example. The inner circumferential surface 20a of the cuff structure 20 is constituted by the first sheet 21A of the sensing cuff 21.

As can be seen from FIGS. 4A and 4B, the pressure cuff 23 includes two fluid bags 23-1 and 23-2 stacked in the thickness direction. Each of the fluid bags 23-1 and 23-2 is formed by facing two stretchable polyurethane sheets (thickness t=0.15 mm) and welding their circumferential portions 23m1 and 23m2. As shown in FIG. 5A, the dimension of the fluid bag 23-1 on the inner circumferential side in the longitudinal direction Y is set to be slightly smaller than the dimension (L2) of the fluid bag 23-2 on the outer circumferential side in the longitudinal direction Y. An end portion on the basal side (+Y side) of the fluid bag 23-2 on the outer circumferential side in the longitudinal direction Y is attached with a flexible tube 39 for supplying a pressure transmission fluid (air in this example) to the pressure cuff 23 or discharging a pressure transmission fluid from the pressure cuff 23. A plurality of (four in this example) through holes 23o, 23o, . . . are formed between the fluid bag 23-1 on the inner circumferential side and the fluid bag 23-2 on the outer circumferential side that is adjacent thereto. This allows the pressurization fluid (air in this example) to flow between the two fluid bags 23-1 and 23-2 through the through holes 23o, 23o, . . . . Thus, when the pressure cuff 23 receives the supply of pressurizing fluid from the main body 10 side through the flexible tube 39 in the attached state, the two stacked fluid bags 23-1 and 23-2 inflate to press the left wrist 90 as a whole.

Figure 12:
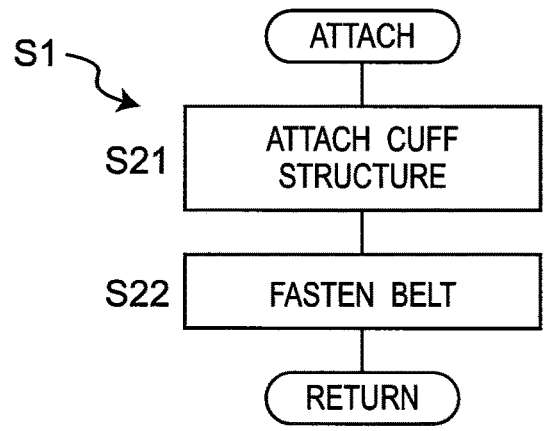
FIG. 12 shows a flow of processing in which a user attaches the sphygmomanometer on the left wrist.

The back plate 22 is made of a plate-shaped resin (polypropylene in this example) having a thickness of about 1 mm in this example. As can be seen from FIGS. 3A and 3B, the back plate 22 extends in a band shape beyond the length of the sensing cuff 21 in the longitudinal direction Y (corresponding to the circumferential direction of the left wrist 90). Accordingly, the back plate 22 acts as a reinforcing plate, and can transmit the pressing force from the pressure cuff 23 to the entire area of the sensing cuff 21 in the longitudinal direction Y (corresponding to the circumferential direction of the left wrist 90). As can be seen from FIGS. 4A and 5B, the inner circumferential surface 22a and the outer circumferential surface 22b of the back plate 22 are provided with a plurality of grooves 22d1 and 22d2 with V-shaped or U-shaped cross sections that extend in the width direction X and are parallel to and spaced apart from each other in the longitudinal direction Y. In this example, the grooves 22d1 and 22d2 are provided at the same position corresponding to each other between the inner circumferential surface 22a and the outer circumferential surface 22b of the back plate 22. As a result, the back plate 22 becomes thinner and easily bent at the locations of the grooves 22d1 and 22d2 compared to other locations. Accordingly, the back plate 22 does not obstruct the cuff structure 20 from being bent along the circumferential direction Y of the left wrist 90 when the user collectively surrounds the left wrist 90 and the cuff structure 20 with the belt 2 (step S22 in FIG. 12 described later) at the time of attaching.

Figure 7:
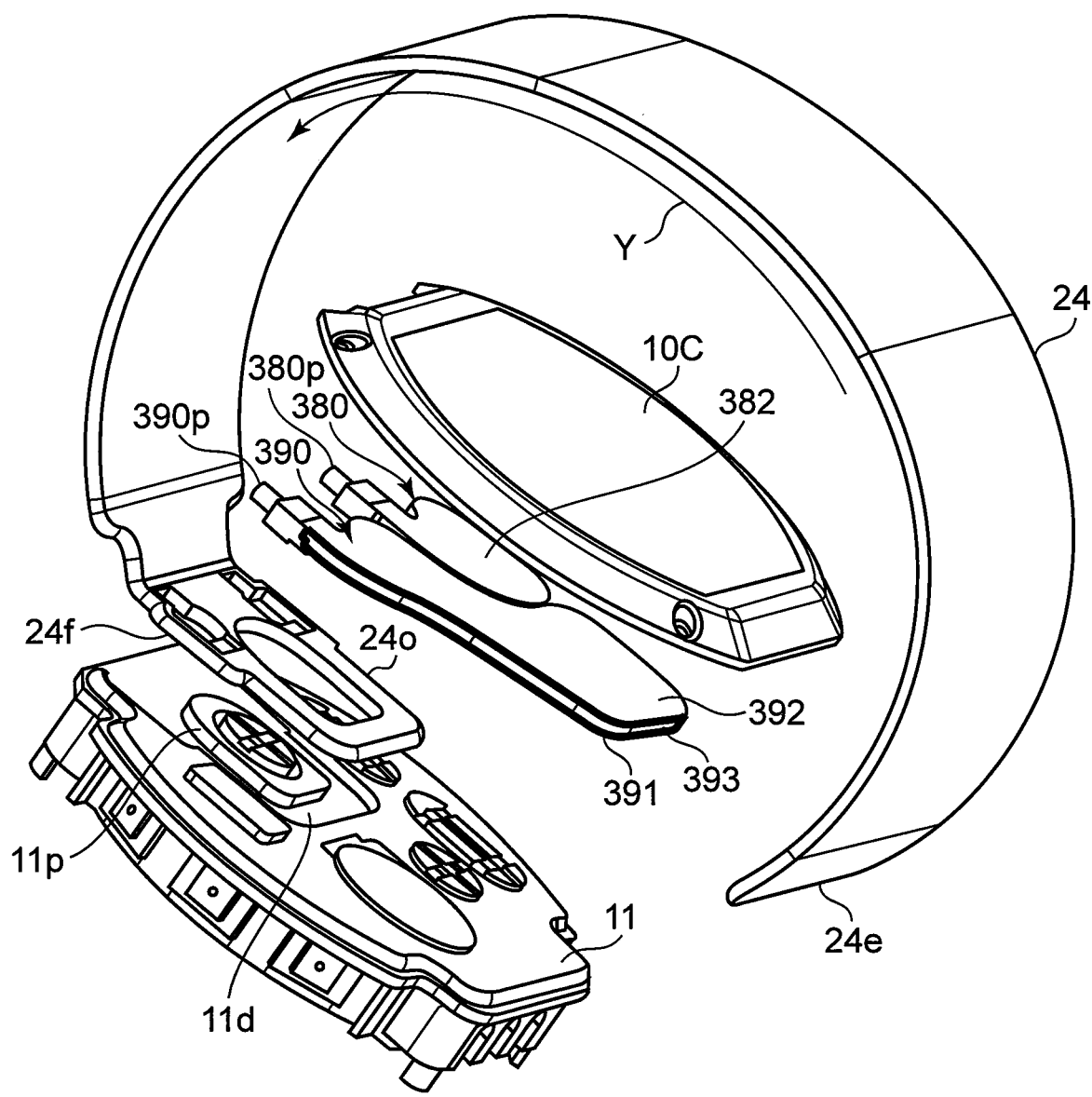
FIG. 7 shows a back side of the main body together with a curler included in the cuff structure described above, in a disassembled state where a back lid is detached.

The curler 24 is made of a resin plate (polypropylene in this example) having a thickness of about 1 mm and having a certain degree of flexibility and hardness in this example. As can be seen from FIGS. 3A and 3B, when unfolded, the curler 24 extends in a band shape beyond the length of the pressure cuff 23 in the longitudinal direction Y (corresponding to the circumferential direction of the left wrist 90). As shown in FIG. 7, the curler 24 has a curved shape along the circumferential direction Y surrounding the left wrist 90 in a natural state. Due to this, the shape of the cuff structure 20 in a natural state is kept curved along the circumferential direction Y of the left wrist 90 as shown in FIG. 2.

At the circumferential portion of the inner circumferential surface 22a of the back plate 22 and the circumferential portion of the inner circumferential surface 24a of the curler 24, circular arcs 22r and 24r curved outwards from the measurement target site (left wrist 90 in this example) are formed respectively. This prevents the user from feeling discomfort due to attachment of the cuff structure 20.

Figure 6:
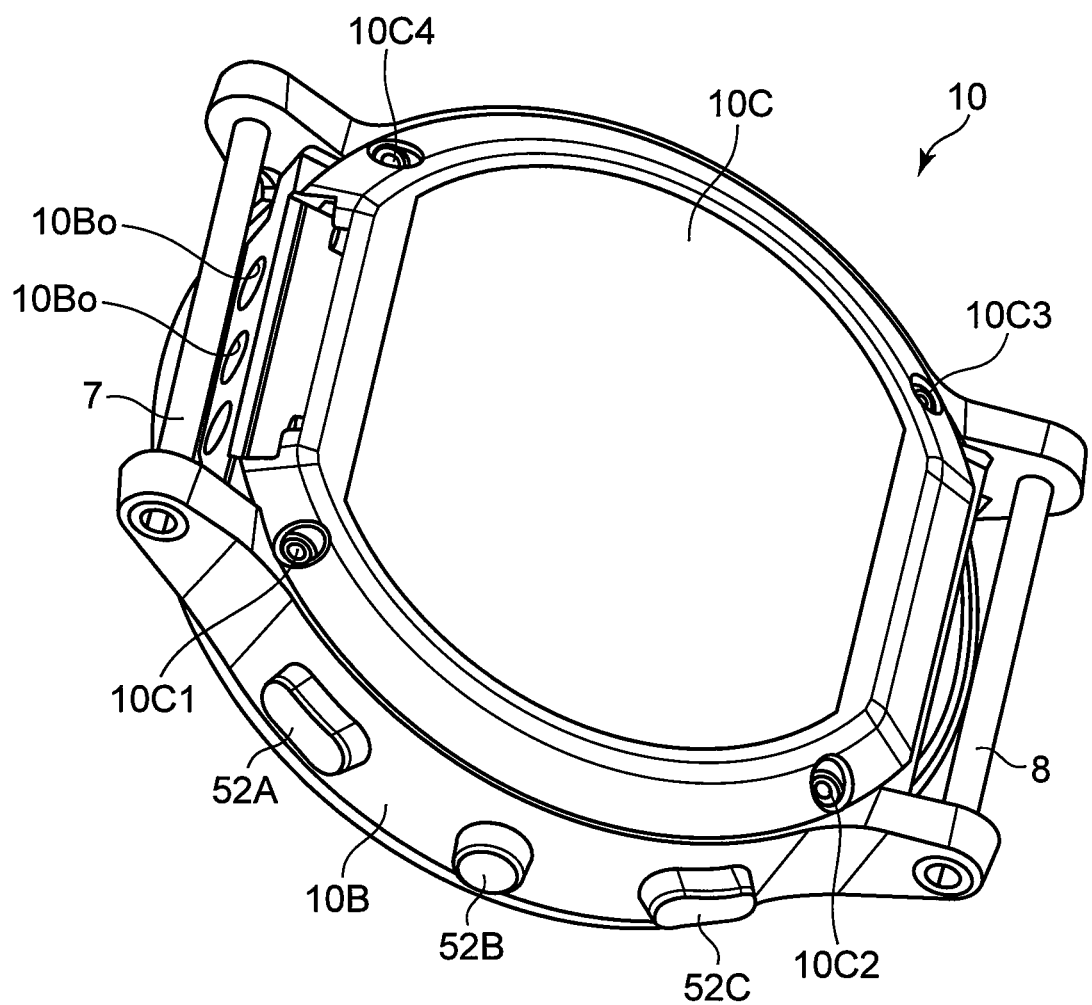
FIG. 6 shows a back side of a main body of the sphygmomanometer as viewed obliquely.

As shown in FIG. 6, the back lid 10C is provided on the back side of the main body 10. The back lid 10C has four through holes 10C1, 10C2, 10C3, and 10C4 and is fixed to the back side of the case 10B with unillustrated screws through the through holes 10C1, 10C2, 10C3, and 10C4. A portion to be hidden by the basal portion 3e of the first belt portion 3 on the side surface of the case 10B is provided with filtered intake and exhaust holes 10Bo, 10Bo, . . . (the same is true for a portion hidden by the basal portion 4e of the second belt portion 4). This allows air to flow between the inside and outside of the case 10B while realizing a life waterproofing function.

FIG. 7 shows the back side of the main body 10 together with the curler 24, in a disassembled state where the back lid 10C is detached. In the case 10B of the main body 10, an inner case member 11 for mounting blood pressure measurement elements is contained. On the back side of the inner case member 11, an annular groove 11d is formed so as to surround a protrusion 11p. A ring 24o having a shape corresponding to the annular groove 11d is formed at the basal portion 24f of the curler 24. When assembling the main body 10, the ring 24o of the basal portion 24f of the curler 24 is fitted into the annular groove 11d of the inner case member 11 (at the same time, the ring 24o is fitted into the protrusion 11p of the inner case member 11). Then the basal portion 24f of the curler 24 is clamped between the back side of the inner case member 11 and the back lid 10C of the main body 10 in a state of being overlapped with two flow path formation members (a first flow path formation member 390 and a second flow path formation member 380) to be described later.

As a result, as shown in FIG. 2, the one end 20f of the cuff structure 20 (the basal portion 24f of the curler 24) is attached to the main body 10. The other end 20e of the cuff structure 20 (a tip end portion 24e of the curler 24) is a free end. As a result, the cuff structure 20 faces the inner circumferential surfaces 3a and 4a of the belt 2 and is freely separable from the inner circumferential surfaces 3a and 4a.

When the cuff structure 20 is attached to the main body 10 in this manner, the one end 20f of the cuff structure 20 is reliably held by the main body 10. At the time of maintenance service, the cuff structure 20 can be replaced with respect to the main body 10 regardless of the belt 2 by opening the back lid 10C of the main body 10. Also, the dimension of the cuff structure 20 in the longitudinal direction Y (corresponding to the circumferential direction of the left wrist 90) can be set to the optimum dimension regardless of the belt 2.

Note that in the sphygmomanometer 1, the main body 10 and the belt 2 are formed separately from each other and the belt 2 is attached to the main body 10, and therefore, during maintenance service, the belt 2 can also be replaced with respect to the main body 10 regardless of the cuff structure 20.

Figure 9:
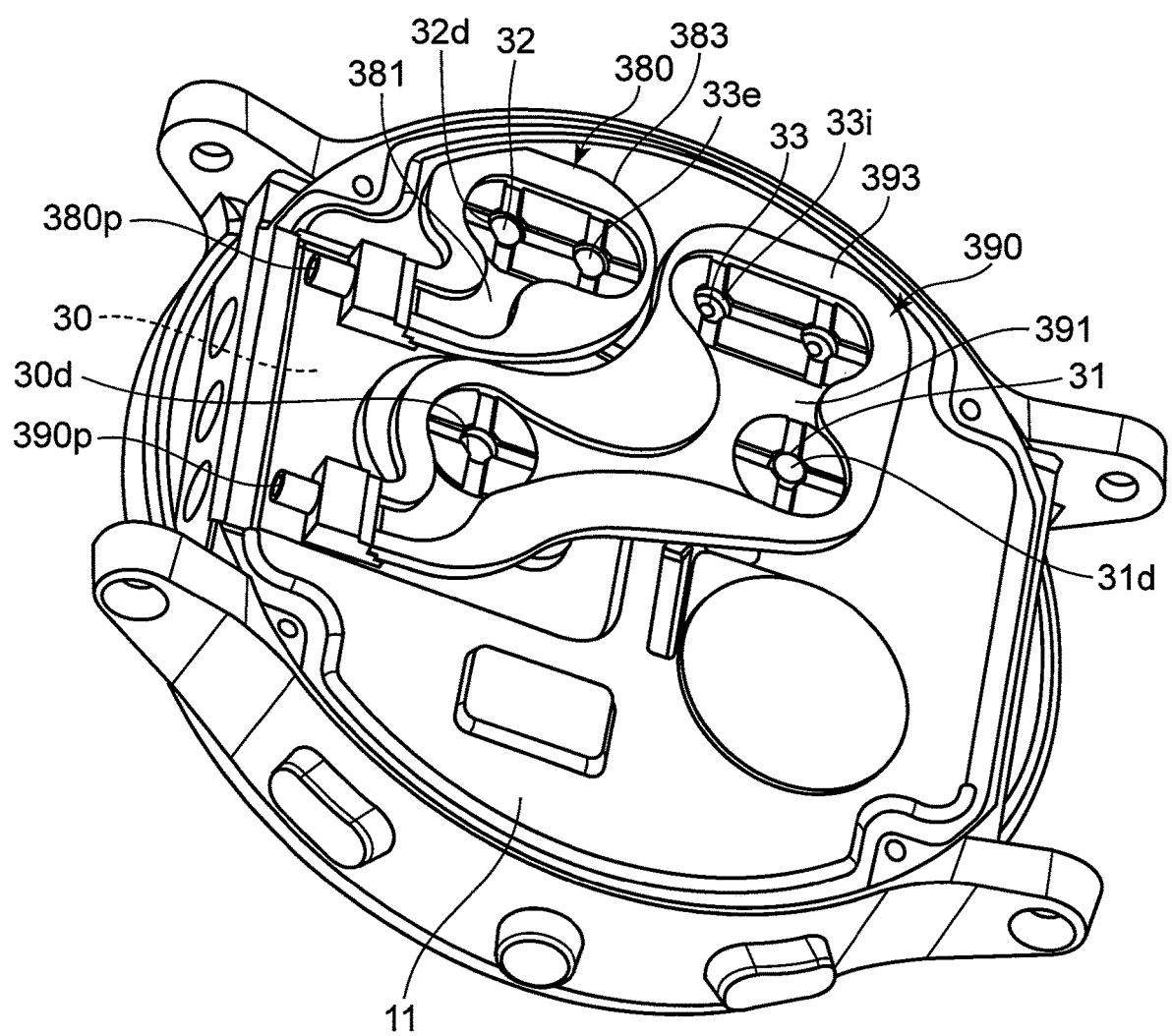
FIG. 9 shows an inside of the main body as viewed obliquely from below.

The first flow path formation member 390 shown in FIG. 7 includes two sheet plates 391 and 392 that expand in a thin plate shape facing each other and a spacer portion 393 that keeps the sheet plates 391 and 392 with a predetermined interval (0.7 mm in this example). Similarly, the second flow path formation member 380 includes two sheet plates 381 and 382 that expand in a thin plate shape facing each other and a spacer portion 383 that keeps the sheet plates 381 and 382 with a predetermined interval. The sheet plate 381 and the spacer portion 383 are shown in FIG. 9 (In FIG. 9, the sheet plates 392 and 382 on the side far from the inner case member 11 are not illustrated for the sake of easy understanding. FIG. 9 will be described later). Laterally oriented pins 390p and 380p are integrally attached to the end portion of the first flow path formation member 390 and the end portion of the second flow path formation member 380, respectively, so as to allow fluid to flow. When the cuff structure 20 including the curler 24 is attached to the main body 10, the flexible tube 39 from the pressure cuff 23 is connected to the first flow path formation member 390 via the laterally oriented pin 390p. The flexible tube 38 from the sensing cuff 21 is connected to the second flow path formation member 380 via the laterally oriented pin 380p.

The first flow path formation member 390 and the second flow path formation member 380 are formed by integrally molding elastomer in this example. The thickness dimension of the first flow path formation member 390 and the second flow path formation member 380 is set to 1.2 mm in this example.

Figure 10:
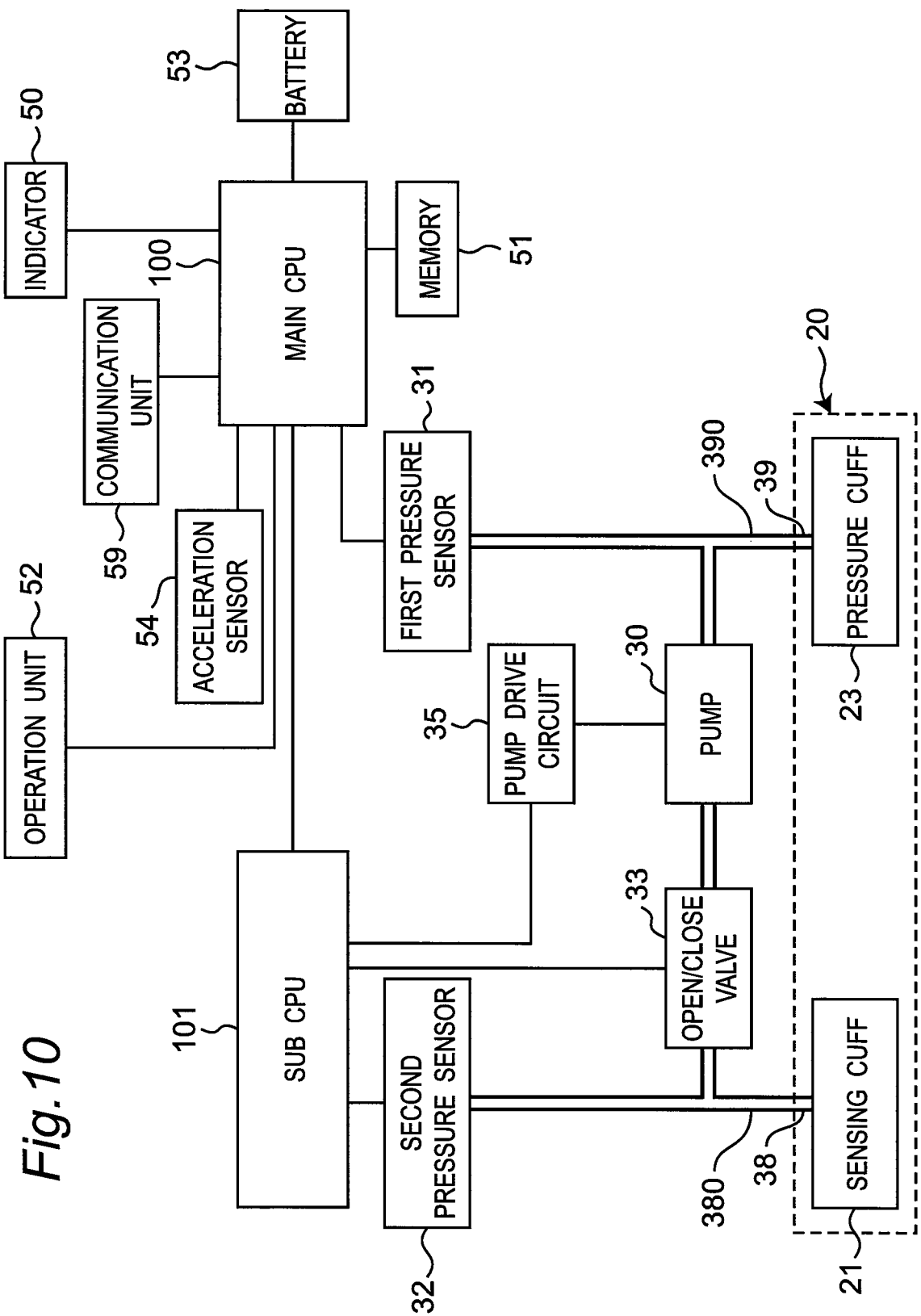
FIG. 10 shows a block configuration of a control system of the sphygmomanometer.

FIG. 10 shows a block configuration of the control system of the sphygmomanometer 1. As blood pressure measurement elements for performing blood pressure measurement in addition to the indicator 50 and the operation unit 52 described above, the main body 10 of the sphygmomanometer 1 is mounted with a main CPU (Central Processing Unit) 100 as a control unit, a sub CPU 101, a memory 51 as a storage unit, an acceleration sensor 54, a communication unit 59, a battery 53, a first pressure sensor 31 for detecting pressure of the pressure cuff 23, a second pressure sensor 32 for detecting pressure of the sensing cuff 21, a pump 30, an open/close valve 33, and a pump drive circuit 35 that drives the pump 30. The main CPU 100 mainly controls the operation of the entire sphygmomanometer 1, and the sub CPU 101 mainly controls an operation of an air system. Hereinafter, for the sake of simplicity, the main CPU 100 and the sub CPU 101 will be simply referred to as the CPU 100 in combination.

The indicator 50 is configured by an LCD (Liquid Crystal Display) in this example and, in accordance with a control signal from the CPU 100, displays information on blood pressure measurement such as a blood pressure measurement result and other information. The indicator 50 is not limited to an organic EL display but may be the indicator 50 of another type such as an organic EL (Electro Luminescence) display. The indicator 50 may include an LED (Light Emitting Diode).

As described above, the operation unit 52 includes the measurement switch 52A for instructing start or stop of blood pressure measurement, the home switch 52B for causing a display screen of the indicator 50 to return to a predetermined home screen, and the recording call switch 52C for performing an instruction of causing the indicator 50 to display measurement records such as past blood pressure and activity amount. In this example, these switches 52A to 52C are push-type switches, and the switches 52A to 52C input operation signals to the CPU 100 in accordance with an instruction by the user such as start or stop of blood pressure measurement. The operation unit 52 is not limited to the push-type switch but may be, for example, a pressure-sensitive (resistive) or proximity (electrostatic capacitive) touch panel-type switch. In addition, an unillustrated microphone may be provided to input an instruction for blood pressure measurement start by the user's voice.

The memory 51 non-transitorily stores data of a program for controlling the sphygmomanometer 1, data used to control the sphygmomanometer 1, setting data for setting various functions of the sphygmomanometer 1, data of measurement results of blood pressure values, and the like. The memory 51 is also used as a work memory or the like when a program is executed.

The CPU 100 executes various functions as a control unit in accordance with a program for controlling the sphygmomanometer 1 stored in the memory 51. For example, when executing a blood pressure measurement function, the CPU 100 performs control to drive the pump 30 and the open/close valve 33 based on signals from the first pressure sensor 31 and the second pressure sensor 32 in response to an instruction of start of blood pressure measurement from the measurement switch 52A of the operation unit 52. The CPU 100 performs control to calculate a blood pressure value, a pulse, and the like based on a signal from the second pressure sensor 32.

The acceleration sensor 54 is configured by a three-axis acceleration sensor integrated in the main body 10. The acceleration sensor 54 outputs, to the CPU 100, an acceleration signal representing the acceleration of the main body 10 in three directions orthogonal to one another. In this example, the output of the acceleration sensor 54 is used to measure the activity amount.

The communication unit 59 is controlled by the CPU 100 to transmit predetermined information to an external device through the network, and receives information from the external device through the network and delivers the information to the CPU 100. The communication via the network may be either wireless or wired. In this embodiment, the network is the Internet but it is not limited thereto, and it may be another type of network such as a hospital LAN (Local Area Network), or it may be a one-to-one communication using a USB cable or the like. The communication unit 59 may include a micro USB connector.

The battery 53 is, in this example, configured by a rechargeable secondary battery. The battery 53 supplies power to elements mounted on the main body 10, which are, in this example, the CPU 100, the memory 51, the acceleration sensor 54, the communication unit 59, the first pressure sensor 31, the second pressure sensor 32, the pump 30, the open/close valve 33, and the pump drive circuit 35.

The pump 30 is configured by a piezoelectric pump in this example, and is driven by the pump drive circuit 35 based on a control signal given from the CPU 100. The pump 30 is connected in fluid communication to the pressure cuff 23 via the first flow path formation member 390 and the flexible tube 39, which constitute a first flow path. The pump 30 can supply air as a pressurizing fluid to the pressure cuff 23 through the first flow path formation member 390 and the flexible tube 39. The pump 30 is mounted with an unillustrated exhaust valve whose opening and closing are controlled in accordance with the on/off of the pump 30. That is, the exhaust valve closes when the pump 30 is turned on to help enclosing of air in the pressure cuff 23, whereas the exhaust valve opens when the pump 30 is turned off to cause the air in the pressure cuff 23 to be discharged to the atmosphere through the flexible tube 39 and the first flow path formation member 390. This exhaust valve has a function of a check valve, and the air to be discharged will never flow back.

The pump 30 is connected in fluid communication to the sensing cuff 21 via the second flow path formation member 380 and the flexible tube 38, which constitute a second flow path. The open/close valve (normally open solenoid valve in this example) 33 is inserted in the second flow path (actually, between the first flow path formation member 390 and the second flow path formation member 380). Opening/closing (opening degree) of the open/close valve 33 is controlled based on a control signal given from the CPU 100. When the open/close valve 33 is in the open state, air can be supplied as a pressure transmission fluid from the pump 30 to the sensing cuff 21 through the second flow path and the sensing cuff 21 is caused to contain the air.

Each of the first pressure sensor 31 and the second pressure sensor 32 is configured by a piezoresistive pressure sensor in this example. The first pressure sensor 31 detects pressure in the pressure cuff 23 via the first flow path formation member 390 and the flexible tube 39, which constitute the first flow path. The second pressure sensor 32 detects pressure in the sensing cuff 21 via the second flow path formation member 380 and the flexible tube 38, which constitute the second flow path.

Figure 8:
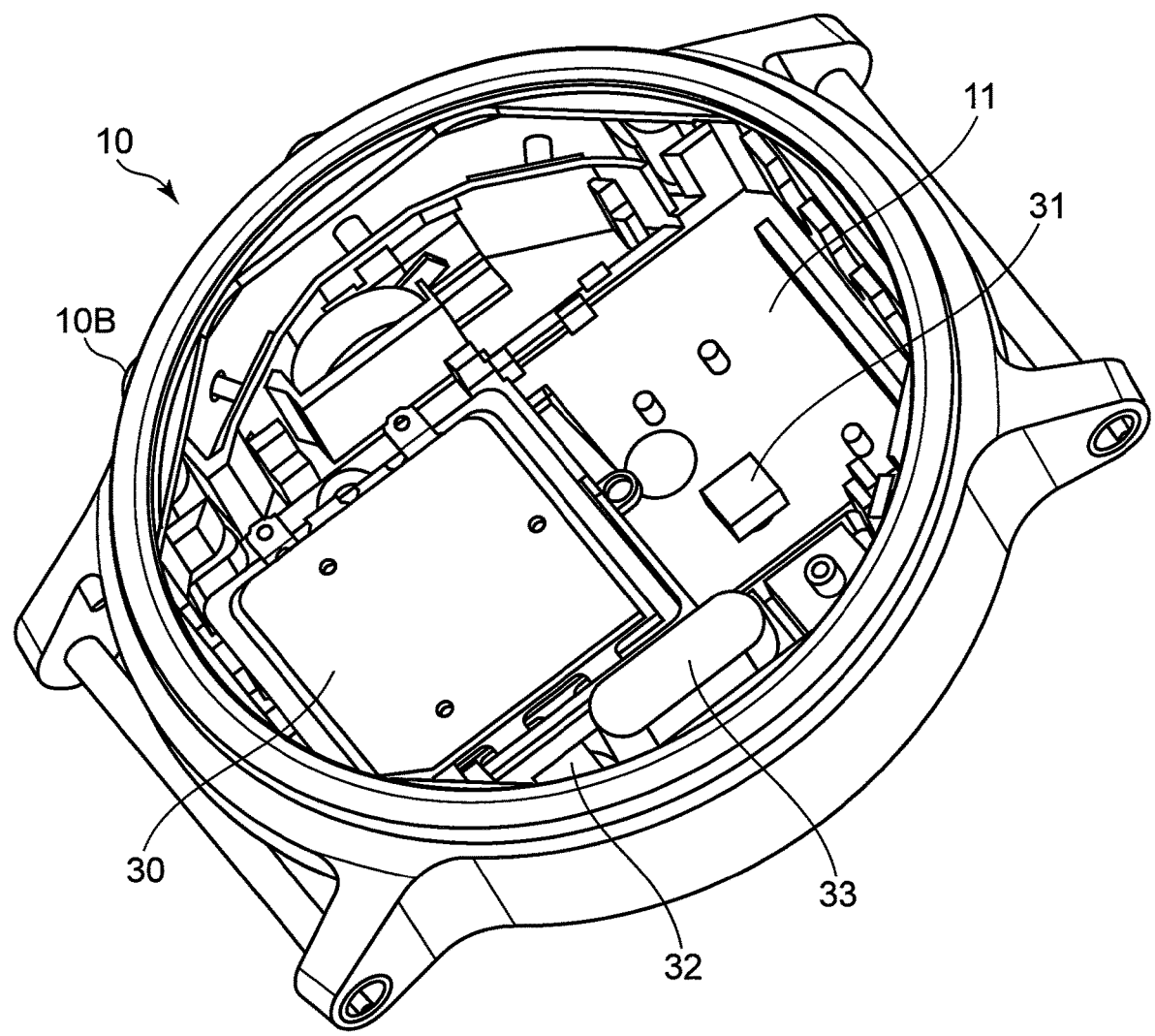
FIG. 8 shows an inside of the main body as viewed obliquely from above.

As shown in FIG. 8 (inside of the main body 10 viewed obliquely from above), the pump 30 and the first pressure sensor 31 are disposed substantially at the center of the inner case member 11 in the main body 10. The open/close valve 33 and the second pressure sensor 32 are disposed around the inner case member 11. As shown in FIG. 9 (inside of the main body 10 viewed obliquely from below), the first flow path formation member 390 is provided on the back side of the inner case member 11 across a discharge port 30d of the pump 30, an air inlet 31d of the first pressure sensor 31, and an inlet 33i of the open/close valve 33. The second flow path formation member 380 is disposed on the back side of the inner case member 11 across an outlet 33e of the open/close valve 33 and an air inlet 32d of the second pressure sensor 32.

The sphygmomanometer 1 is configured to be compact and integrated by mounting the blood pressure measurement elements described above on the main body 10. Accordingly, the usability for the user is good.

(Operation of Blood Pressure Measurement)

Figure 11:
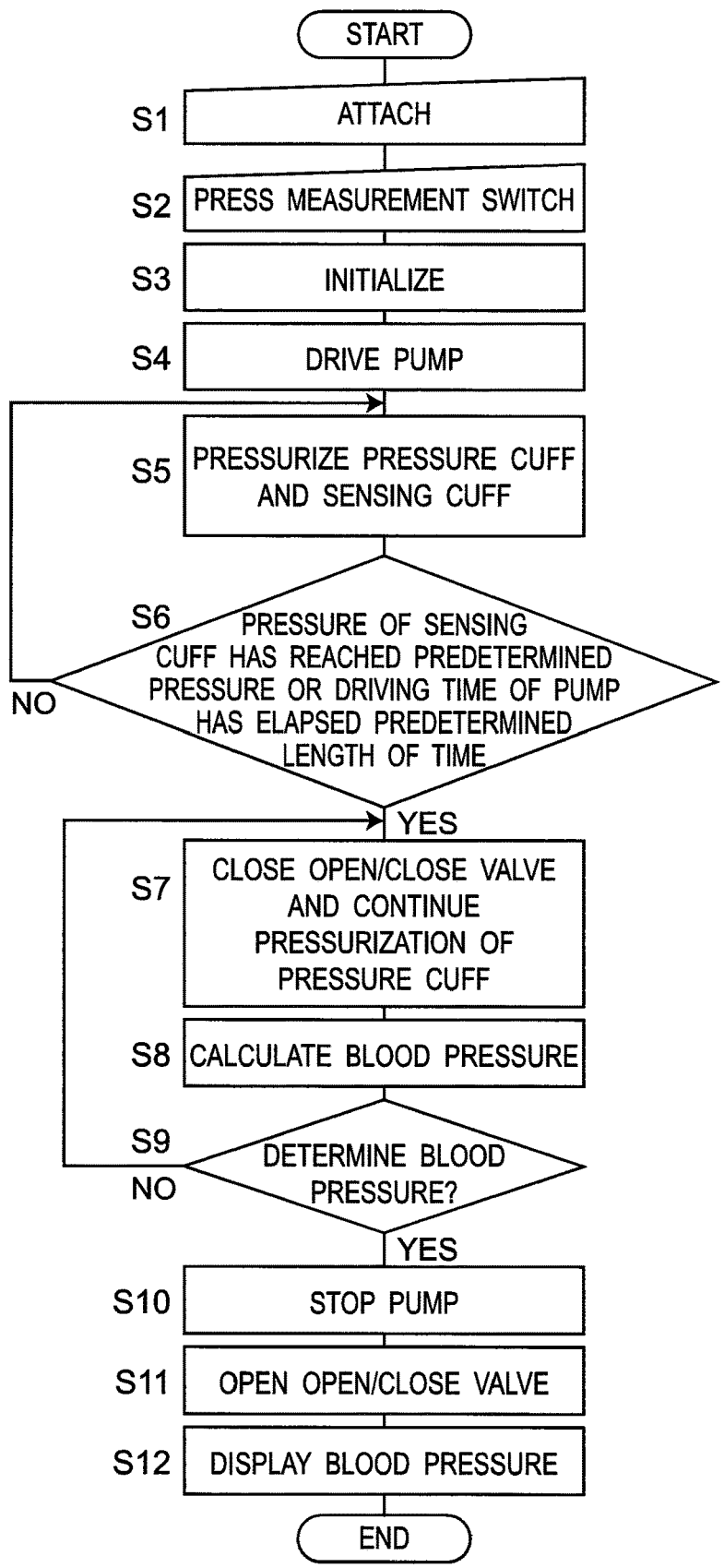
FIG. 11 shows an operation flow when a user performs blood pressure measurement using the sphygmomanometer as a blood pressure measurement method according to an embodiment of the present invention.

FIG. 11 shows an operation flow when the user performs blood pressure measurement using the sphygmomanometer 1 as a blood pressure measurement method according to an embodiment of the present invention.

As shown in step S1 of FIG. 11, the user attaches the sphygmomanometer 1 on the left wrist 90 as a measurement target site. At the time of this attachment, as shown in FIG. 13A, the user first attaches the cuff structure 20 to the left wrist 90 using a right hand 99 (step S21 in FIG. 12). Here, the cuff structure 20 is curved along the circumferential direction Y of the left wrist 90 by the curler 24 in a natural state. Accordingly, in this example, the user can easily attach the cuff structure 20 to the left wrist 90 by fitting the cuff structure 20 on the outer circumferential surface of the left wrist 90 using the hand (the right hand 99 in this example) on the right side of the body, which is opposite to the left side of the body to which the left wrist 90 belongs. With the cuff structure 20 attached to the left wrist 90, the cuff structure 20 holds the left wrist 90 even if the user releases the right hand 99 from the cuff structure 20, and hence the cuff structure 20 (as well as the belt 2 and the main body 10) is unlikely to come off from the left wrist 90.

Next, as shown in FIG. 13B, the user uses the right hand 99 to collectively surround the left wrist 90 and the cuff structure 20 with the belt 2. Specifically, the user passes a portion continuing to the tip end portion 4f of the second belt portion 4 through the frame 5A of the clasp 5 of the first belt portion 3, and inserts the prong 5B of the clasp 5 into any one of the plurality of small holes 4w, 4w, . . . of the second belt portion 4. Thus, as shown in FIG. 13C, the first belt portion 3 and the second belt portion 4 are fastened (step S22 in FIG. 12). Due to this, the belt 2 extending from the main body 10 surrounds the left wrist 90, and the band-shaped cuff structure 20 having the one end 20f attached to the main body 10 is disposed on the inner circumferential side closer to the left wrist 90 than the belt 2 is.

Here, in the sphygmomanometer 1, the cuff structure 20 is freely separable from the inner circumferential surfaces 3a and 4a of the belt 2, and the other end 20e on the side opposite to the one end 20f of the cuff structure 20 is a free end. Accordingly, when fastening the first belt portion 3 and the second belt portion 4, the cuff structure 20 receives an inward force from the belt 2, and the cuff structure 20 can slide or deform so as to exactly follow the outer circumferential surface of the left wrist 90. Thus, in the attached state, the cuff structure 20 and the belt 2 are substantially in close contact in this order with the outer circumferential surface of the left wrist 90, in other words, the cuff structure 20 and the belt 2 surround the left wrist 90 in a band shape as a whole. In this manner, the sphygmomanometer 1 can be easily attached to the left wrist 90.

Figure 14:
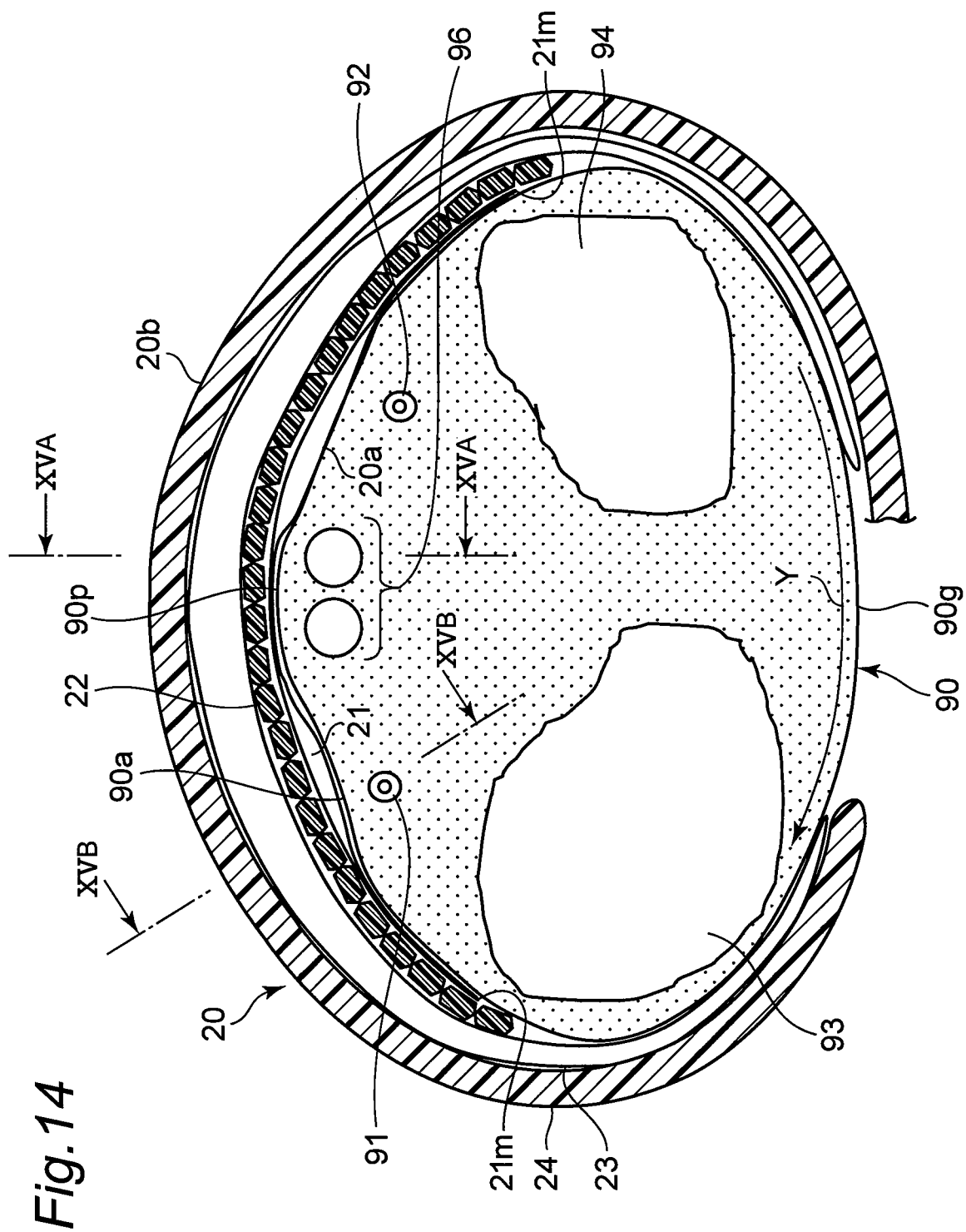
FIG. 14 shows a cross section perpendicular to the left wrist, with the sphygmomanometer attached to the user's left wrist.

Specifically, as shown in FIG. 14, in this attached state, the bag-shaped pressure cuff 23 extends along the circumferential direction Y of the left wrist 90 on the inner circumferential side of the curler 24 included in the cuff structure 20. In addition, the bag-shaped sensing cuff 21 included in the cuff structure 20 is disposed on the inner circumferential side of the pressure cuff 23 to be in contact with the left wrist 90 and extends in the circumferential direction Y across an artery passing portion 90a of the left wrist 90. The back plate 22 included in the cuff structure 20 is inserted between the pressure cuff 23 and the sensing cuff 21 and extends along the circumferential direction Y of the left wrist 90. In FIG. 14, the main body 10 and the belt 2 are not illustrated. FIG. 14 shows a radius 93, an ulna 94, a radial artery 91, an ulnar artery 92, and a tendon 96 of the left wrist 90.

Next, when the user presses the measurement switch 52A of the operation unit 52 provided in the main body 10 (step S2 in FIG. 11), the CPU 100 initializes the processing memory area (step S3 in FIG. 11). The CPU 100 turns off the pump 30 via the pump drive circuit 35, opens the exhaust valve built in the pump 30, and maintains the open/close valve 33 in the open state, so that the air in the pressure cuff 23 and the sensing cuff 21 is exhausted. Then, the CPU 100 performs control of adjusting 0 mmHg of the first pressure sensor 31 and the second pressure sensor 32.

Next, the CPU 100, which serves as a pressurization control unit and a fluid containment control unit, turns on the pump 30 via the pump drive circuit 35 (step S4 in FIG. 11), maintains the open/close valve 33 in the open state, and starts pressurization of the pressure cuff 23 and the sensing cuff 21 (step S5 in FIG. 11). In the pressurization process, the pump 30 is driven via the pump drive circuit 35 while monitoring the pressure of the pressure cuff 23 and the sensing cuff 21 by the first pressure sensor 31 and the second pressure sensor 32, respectively. As a result, the CPU 100 performs control of sending air to the pressure cuff 23 through the first flow path (the first flow path formation member 390 and the flexible tube 39) and to the sensing cuff 21 through the second flow path (the second flow path formation member 380 and the flexibile tube 38).

Next, in step S6 of FIG. 11, the CPU 100, which serves as a fluid containment control unit, determines whether the pressure of the sensing cuff 21 has reached a predetermined pressure (15 mmHg in this example) or whether the driving time of the pump 30 has elapsed a predetermined length of time (3 seconds in this example). The reason for making this determination is to confirm whether an appropriate amount of air has been contained in the sensing cuff 21. If NO in step S6 of FIG. 11, the process waits for the pressure of the sensing cuff 21 to reach a predetermined pressure or the driving time of the pump 30 to elapse a predetermined length of time. The amount of an "appropriate amount" of the pressure transmission fluid contained in the sensing cuff 21 will be described later.

Figure 16:
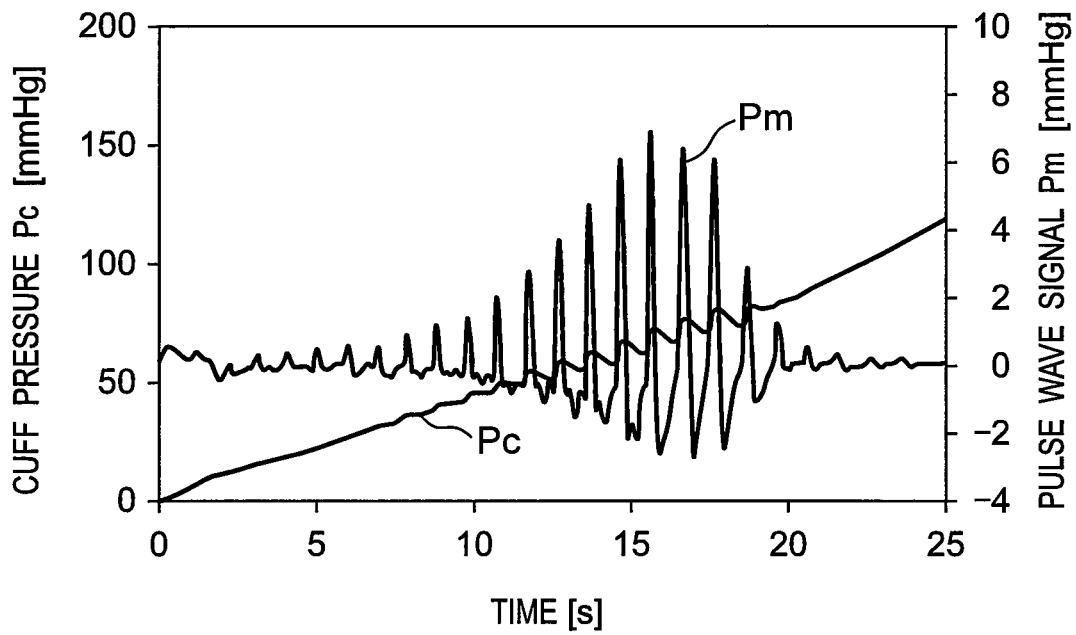
FIG. 16 is a view exemplifying a pressure Pc of a sensing cuff and a pulse wave signal Pm which are detected by a second pressure sensor mounted on the main body.

If YES in step S6 of FIG. 11, it is determined that an appropriate amount of air has been contained in the sensing cuff 21. Then, in step S7 of FIG. 11, the CPU 100, which serves as a pressurization control unit, closes the open/close valve 33, and continues control of supplying air from the pump 30 to the pressure cuff 23 through the first flow path. With this, the pressure cuff 23 is caused to inflate and gradually pressurized to press the left wrist 90. At this time, the back plate 22 transmits the pressing force from the pressure cuff 23 to the sensing cuff 21. The sensing cuff 21 presses the left wrist 90 (including the artery passing portion 90a). In this pressurization process, in order to calculate the blood pressure value, the CPU 100, using the second pressure sensor 32, monitors the pressure Pc of the sensing cuff 21, that is, the pressure of the artery passing portion 90a of the left wrist 90, and obtains the pulse wave signal Pm as a variation component. FIG. 16 exemplifies the pressure Pc and the waveform of the pulse wave signal Pm of the sensing cuff 21 obtained in this pressurization process.

Figure 15A:
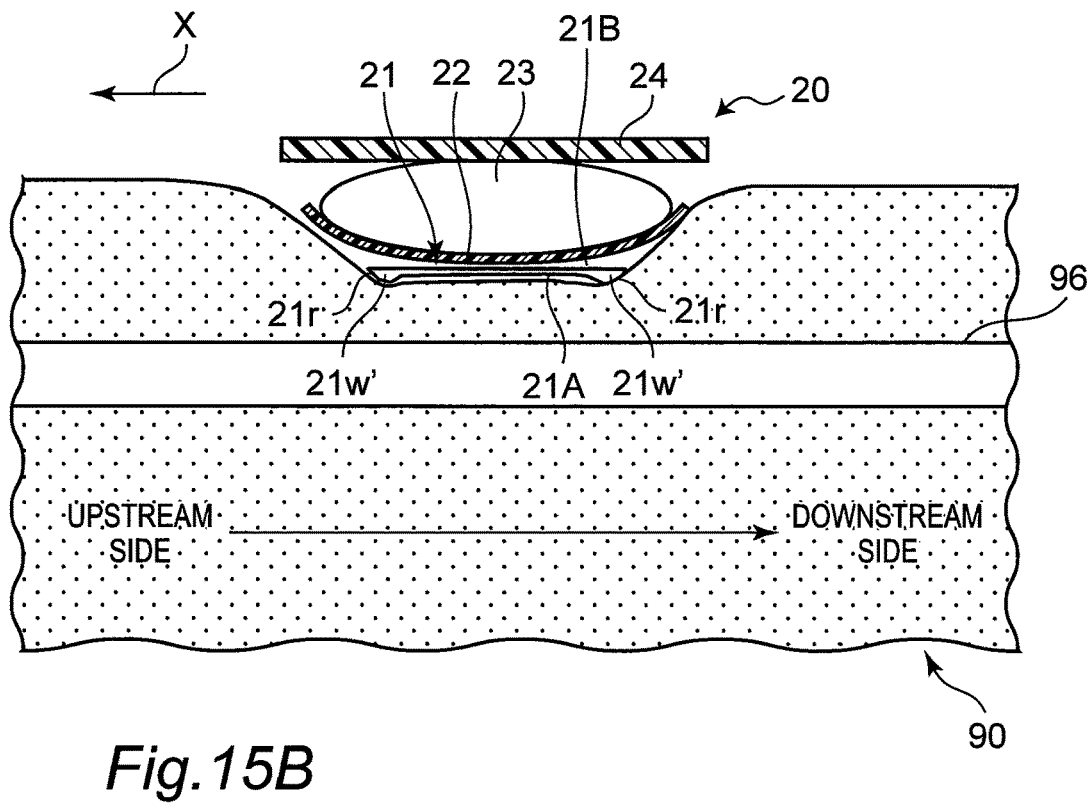
FIG. 15A shows a cross section (corresponding to a cross section taken along line XVA-XVA in FIG. 14) of a portion through which a tendon of a left wrist passes, in a pressurized state.
Figure 15B:
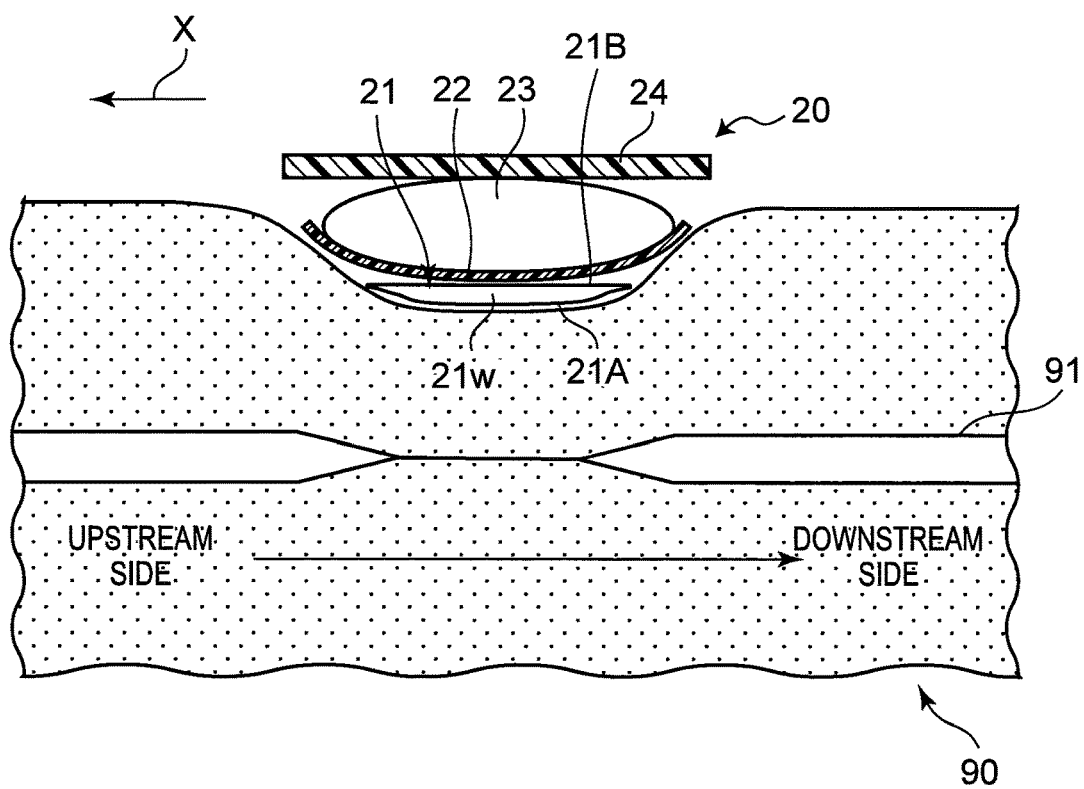
FIG. 15B shows a cross section (corresponding to a cross section taken along line XVB-XVB in FIG. 14) of a portion through which a radial artery of a left wrist passes, in a pressurized state.

Here, FIGS. 15A and 15B schematically show a cross section along the longitudinal direction of the left wrist 90 (corresponding to the width direction X of the cuff) with an appropriate amount of air contained in the sensing cuff 21 and the open/close valve 33 closed. FIG. 15A shows a cross section (corresponding to a cross section taken along line XVA-XVA in FIG. 14) of a portion through which the tendon 96 of the left wrist 90 passes. On the other hand, FIG. 15B shows a cross section (corresponding to a cross section taken along line XVB-XVB in FIG. 14) of a portion through which the radial artery 91 of the left wrist 90 passes. As shown in FIG. 15B, the portion through which the radial artery 91 of the left wrist 90 passes is relatively soft, and hence a gap 21w in which air is present remains between the first sheet 21A and the second sheet 21B of the sensing cuff 21. Accordingly, a portion of the sensing cuff 21 facing the radial artery 91 can reflect the pressure of the artery passing portion 90a of the left wrist 90. On the other hand, as shown in FIG. 15A, since the portion through which the tendon 96 of the left wrist 90 passes is relatively hard, the first sheet 21A and the second sheet 21B are in contact with each other in a portion corresponding to substantially the center of the sensing cuff 21 in the width direction X. However, the slacks 21r and 21r that extend along the longitudinal direction Y (corresponding to the circumferential direction of the left wrist 90) as described above are provided at a location continuing to the edge portions 21m and 21m on both sides of the sensing cuff 21 in the width direction X, and hence gaps 21w' and 21w' in which air present remain along the longitudinal direction Y. As a result, the air contained in the sensing cuff 21 can flow along the longitudinal direction Y of the sensing cuff 21 through the gaps 21w' and 21w'. Accordingly, the sensing cuff 21 can successfully transmit the pressure applied to the artery passing portion 90a of the left wrist 90 to the second pressure sensor 32 in the main body 10 as the pressure of air (pressure transmission fluid).

Next, in step S8 of FIG. 11, the CPU 100, which serves as a blood pressure calculation unit, attempts to calculate the blood pressure value (a systolic blood pressure SBP and a diastolic blood pressure DBP) by applying a publicly known algorithm with the oscillometric method based on the pulse wave signal Pm having been acquired at this point of time.

At this point of time, if the blood pressure value cannot be calculated because of data insufficiency (NO in step S9), the processes of steps S7 to S9 are repeated unless the cuff pressure has reached the upper limit pressure (for safety, it is predetermined as 300 mmHg for example).

When the blood pressure value can be calculated (YES in step S9) in this manner, the CPU 100 performs control of stopping the pump 30 (step S10), opening the open/close valve 33 (step S11), and exhausting the air in the pressure cuff 23 and the sensing cuff 21. Finally, the measurement result of the blood pressure value is displayed on the indicator 50 (step S12).

The blood pressure calculation may be performed not in the pressurization process but in the depressurization process of the pressure cuff 23.

As described above, in the sphygmomanometer 1, air is contained in the sensing cuff 21 each time the blood pressure is measured, and, separately from the pressure cuff 23, the second pressure sensor 32 detects the pressure Pc of the sensing cuff 21, i.e., the pressure itself of the artery passing portion (including both the radial artery 91 and the ulnar artery 92) 90a of the left wrist 90. Accordingly, the blood pressure can be accurately measured, even if the pressure cuff 23 greatly inflates in the thickness direction when pressurized and press loss occurs as a result of setting the dimension of the width direction X of the belt 2 and the cuff structure 20 (simply collectively referred to as "cuff" as appropriate) to be small (about 25 mm for example). In the attached state, the sensing cuff 21 extends in the circumferential direction Y across the artery passing portion 90a of the left wrist 90. Accordingly, when the user actually attaches the sphygmomanometer 1 on the left wrist 90, the sensing cuff 21 will not come off from the left wrist 90 at the artery passing portion 90a even if the cuff, together with the main body 10, is displaced to a certain extent in the circumferential direction Y of the left wrist 90. Accordingly, it is possible to prevent the blood pressure measurement value from varying with respect to the actual blood pressure, and as a result, it is possible to accurately measure the blood pressure.

While in the above example, the air as the pressure transmission fluid is contained in the sensing cuff 21 each time the blood pressure is measured and the air is exhausted after the measurement is completed, the present invention is not limited thereto. The pressure transmission fluid may be contained and sealed in the sensing cuff 21 at the manufacturing stage of the sphygmomanometer 1.

(Appropriate Amount of Pressure Transmission Fluid Contained in Sensing Cuff)

Figure 17:
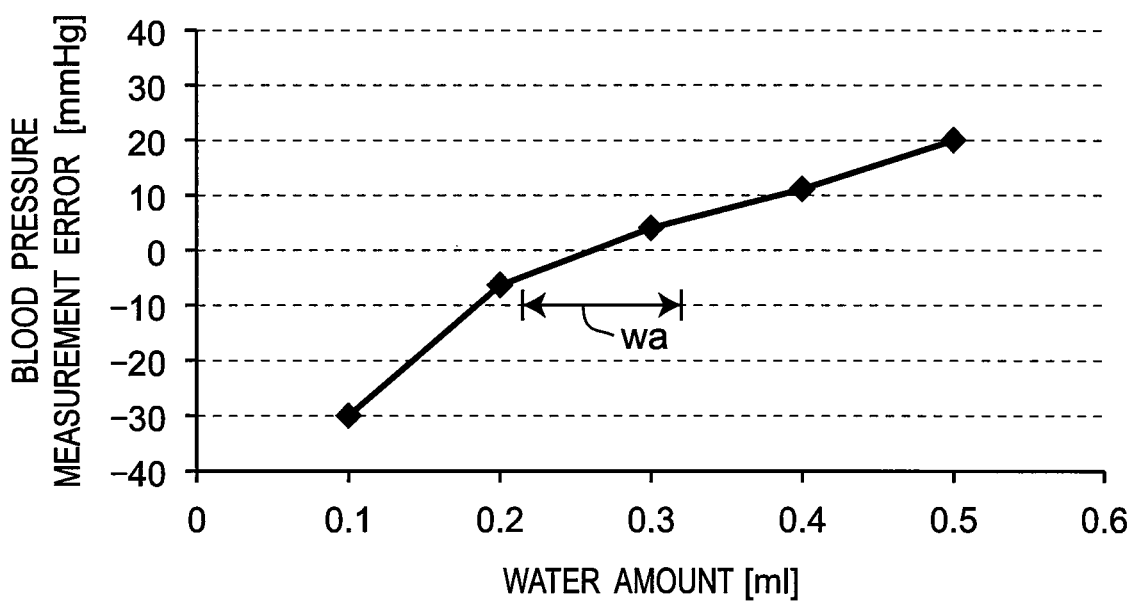
FIG. 17 shows a blood pressure measurement error when water is used as a pressure transmission fluid contained in the sensing cuff and an amount of water contained in the sensing cuff is set variably.

FIG. 17 shows a blood pressure measurement error (average value) when water is used as the pressure transmission fluid contained in the sensing cuff 21 and the amount of water contained in the sensing cuff 21 is set variably. Here, the blood pressure measurement error means a difference obtained by subtracting a blood pressure value measured by a standard (accurate) sphygmomanometer (systolic blood pressure SBP) (this is called "reference blood pressure value") from a blood pressure value measured by the sphygmomanometer 1 (systolic blood pressure SBP) for a certain user (subject). That is, (blood pressure measurement error)=(blood pressure value measured by sphygmomanometer 1)− (reference blood pressure value).

As can be seen from FIG. 17, if the amount of water contained in the sensing cuff 21 is within a range wa of 0.26 ml±0.05 ml, the blood pressure measurement error is within ±5 mmHg, which is considered to be an appropriate amount.

In FIG. 17, if the amount of water exceeds the appropriate amount range wa, the blood pressure measurement error increases to the positive side. This is because the water intervening also on the hard portion such as the tendon 96 in the cross section shown in FIG. 14 raises the internal pressure of the sensing cuff 21 when pressed, and since the portion of the left wrist 90 through which the radial artery 91 and the ulnar artery 92 pass is relatively soft, the presence of water in the portion more than necessary causes the sensing cuff 21 to inflate and the internal pressure of the sensing cuff 21 increases by the amount of the tension that inflates the sensing cuff 21. In FIG. 17, when the amount of water falls below the appropriate amount range wa, the blood pressure measurement error increases to the negative side. This is considered because the amount of water around the artery becomes too small.

As a result, in this example, the range wa of 0.26 ml±0.05 ml is considered to be appropriate for the pressure transmission fluid contained in the sensing cuff 21. The criteria described above in step S6 of FIG. 11 for determining whether the pressure of the sensing cuff 21 has reached a predetermined pressure (15 mmHg in this example) or whether the driving time of the pump 30 has elapsed a predetermined length of time (3 seconds in this example) has been set so as to satisfy the condition that the amount of air as a pressure transmission fluid contained in the sensing cuff 21 falls within the range wa of 0.26 ml±0.05 ml.

As a matter of course, the appropriate amount of the pressure transmission fluid contained in the sensing cuff 21 depends on the size of the sensing cuff 21 and the like.

(Verification Result)

Figure 18:
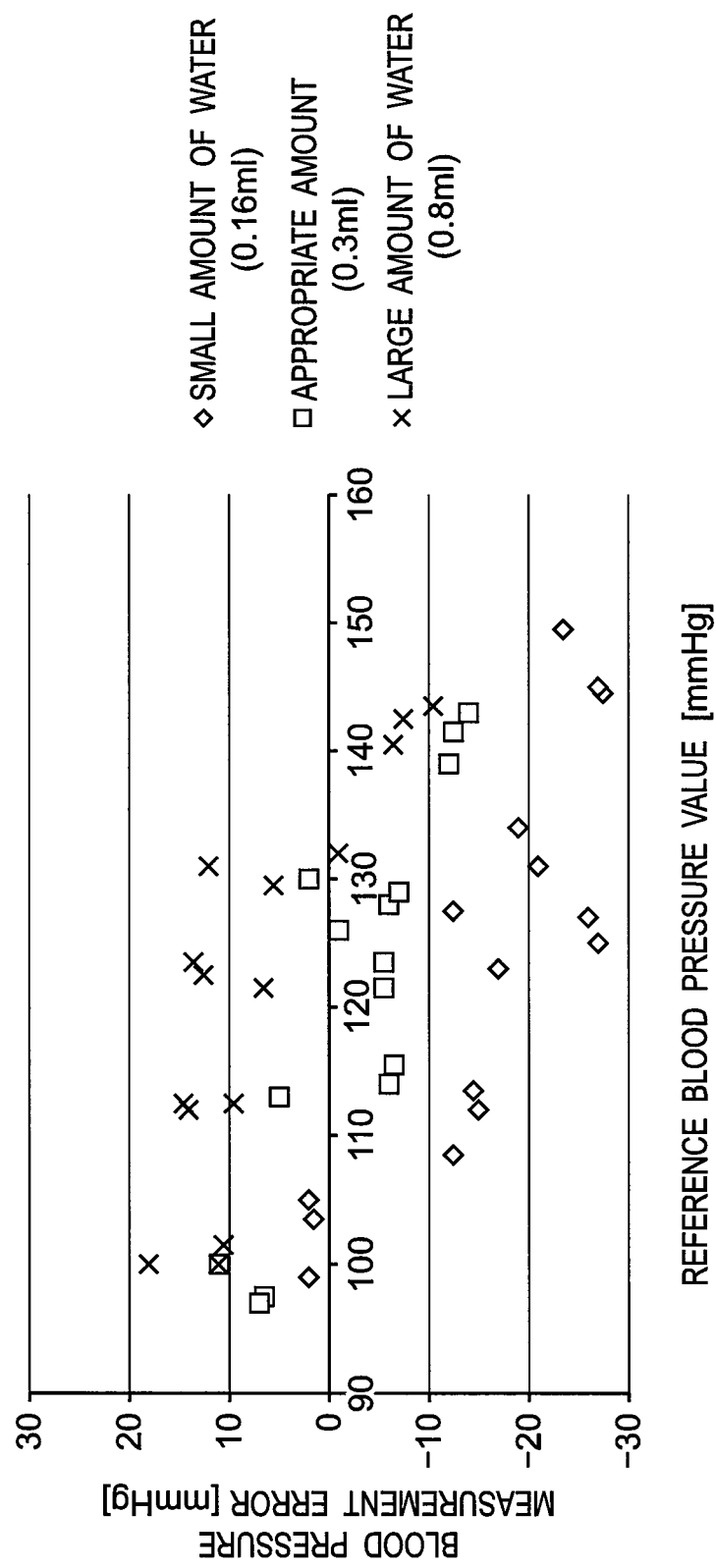
FIG. 18 is a scatter diagram showing a relationship between a reference blood pressure value and a blood pressure measurement error in a case where an amount of water contained in the sensing cuff is set variably to "small amount of water"=0.16 ml, "appropriate amount"=0.3 ml, and "large amount of water"=0.8 ml for a plurality of users.

The scatter diagram in FIG. 18 shows a relationship between the reference blood pressure value and the blood pressure measurement error in the case where the amount of water as a pressure transmission fluid contained in the sensing cuff 21 is set variably to "small amount of water"=0.16 ml, "appropriate amount"=0.3 ml, and "large amount of water"=0.8 ml for a plurality of users (in this example, measurement is performed three times for each of five subjects whose systolic blood pressure SBP is from 97 mmHg to 149 mmHg). If the amount of water is the "appropriate amount", the blood pressure measurement error is small for the plurality of users as shown by the square mark (□) in the figure. On the other hand, in case of the "large amount of water", the blood pressure measurement error is large to the positive side for the plurality of users as shown by the cross mark (x) in the figure. In case of the "small amount of water", the blood pressure measurement error is large on the negative side for the plurality of users as shown by the rhomboid mark (◇) in the figure.

This verification result indicates that according to the sphygmomanometer 1 of the present invention, the blood pressure can be measured accurately even if the dimension of the width direction X of the cuff is set small (in this example, the substantial width direction dimension of the sensing cuff 21 is W4=15 mm, and the substantial width direction dimension of the pressure cuff 23 is set to W2=25 mm).

In particular, when a plurality of users each actually attach the sphygmomanometer 1 on the left wrist 90 to measure the blood pressure, for some users, the cuff, together with the main body 10, may be displaced to a certain extent in the circumferential direction Y of the left wrist 90. Here, in the verification result of FIG. 18, if the amount of water is appropriate, the blood pressure measurement errors are suppressed for the plurality of users. Accordingly, it can be confirmed that with this sphygmomanometer 1, the blood pressure can be measured accurately even if the cuff, together with the main body 10, is displaced to a certain extent in the circumferential direction Y of the left wrist 90.

(How to Set the Length of the Cuff Structure)

Figure 19:
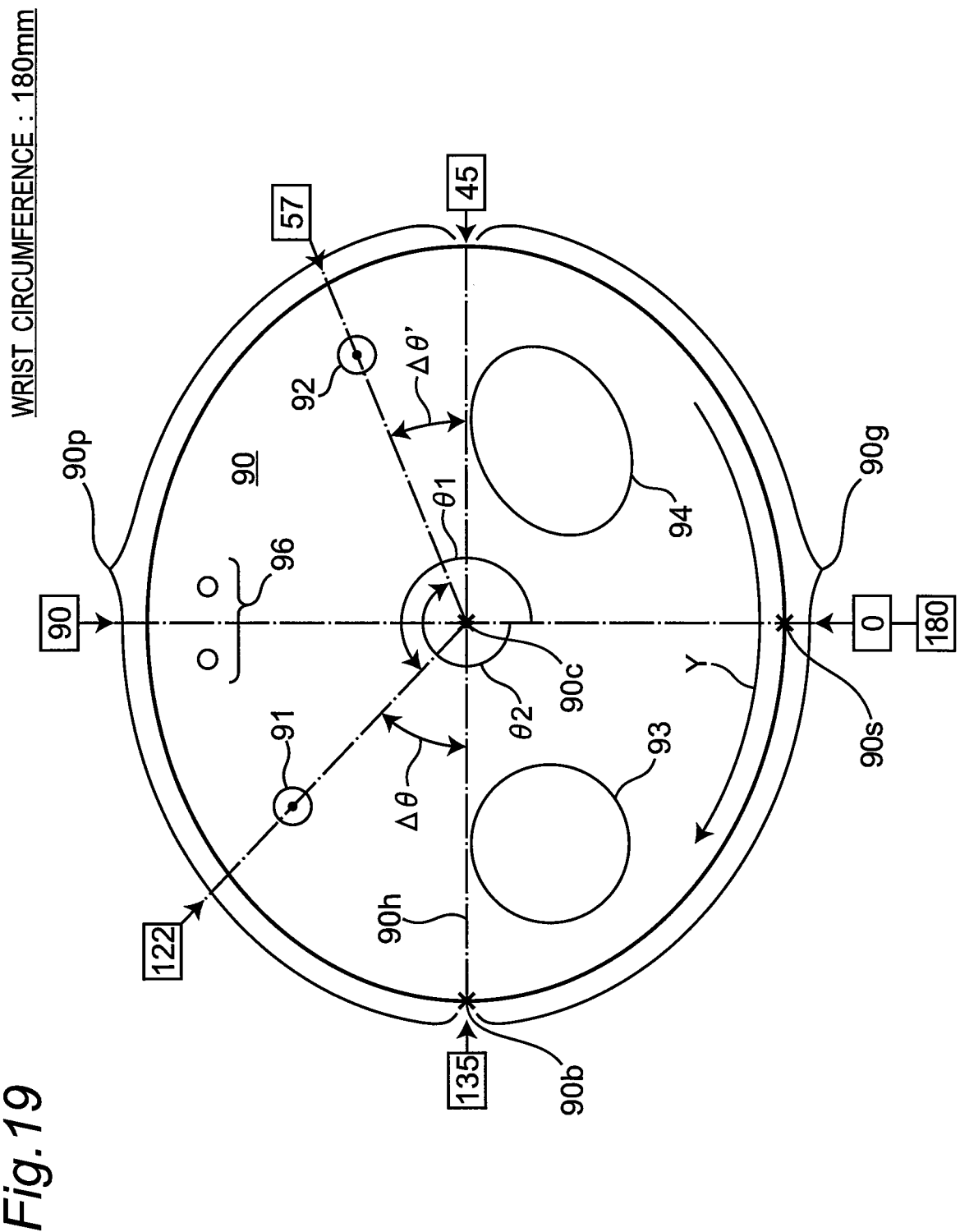
FIG. 19 is a cross-sectional view schematically showing a structure of a left wrist as a measurement target site.

FIG. 19 schematically shows a cross-sectional structure of the left wrist 90 as a measurement target site. Similarly to FIG. 14, FIG. 19 shows the radius 93, the ulna 94, the radial artery 91, the ulnar artery 92, and the tendon 96 of the left wrist 90. Here, in the left wrist 90, a semi-circumferential surface corresponding to the back side of the hand is referred to as a dorsal surface 90g, and a semi-circumferential surface corresponding to the palm side of the hand is referred to as a palmar surface 90p. In this example, the left wrist 90 is assumed to have an average wrist circumference of 180 mm. The numbers (0, 45, 57, 90, 122, 135, and 180 in this example) each enclosed by a square frame given around the ellipse representing the left wrist 90 in FIG. 19 represent circumferential length measured in the counter-clockwise direction (in FIG. 19) along the circumferential direction Y of the left wrist 90 from the center 90s of the dorsal surface 90g (similarly in FIGS. 20 to 22 described later). The circumferential length of the left wrist 90 from the center 90s of the dorsal surface 90g becomes 180 mm, returning to the center 90s of the dorsal surface 90g. As described above, the inventor has focused on the fact that, in the cross section of the left wrist 90, there is a magnitude relationship $\Delta\theta > \Delta\theta'$ with respect to the angles $\Delta\theta$ and $\Delta\theta'$ when the radial artery 91 and the ulnar artery 92 are viewed respectively from the center 90c of the wrist, with the boundary surface 90h between the dorsal surface 90g and the palmar surface 90p as a reference. Accordingly, the counterclockwise (in FIG. 19) angle $\theta 1$ (and the circumferential length) from the center 90s of the dorsal surface 90g to the radial artery 91 is smaller than the clockwise (in FIG. 19) angle $\theta 2$ (and the circumferential length) from the center 90s of the dorsal surface 90g to the ulnar artery 92. This means that the length of the cuff structure 20, in particular, the lengths of the pressure cuff 23 and the sensing cuff 21 can be set shorter when covering the radial artery 91 beyond the ulnar artery 92 with the cuff structure 20 extending counterclockwise (in FIG. 19) along the circumferential direction of the wrist from the ulnar side end portion (the end portion on a side close to the ulna 94, which corresponds to the end portion on a side where the lugs 10B1 and 10B2 in FIGS. 1 and 2 are provided) of the main body 10 (disposed on the dorsal surface 90g) as compared to when covering the ulnar artery 92 beyond the radial artery 91 with the cuff structure 20 extending clockwise (in FIG. 19) along the circumferential direction of the wrist from the radial side end portion (the end portion on a side close to the radius 93, which corresponds to the end portion on a side where the lugs 10B3 and 10B4 in FIGS. 1 and 2 are provided) of the main body, conversely.

Figure 20:
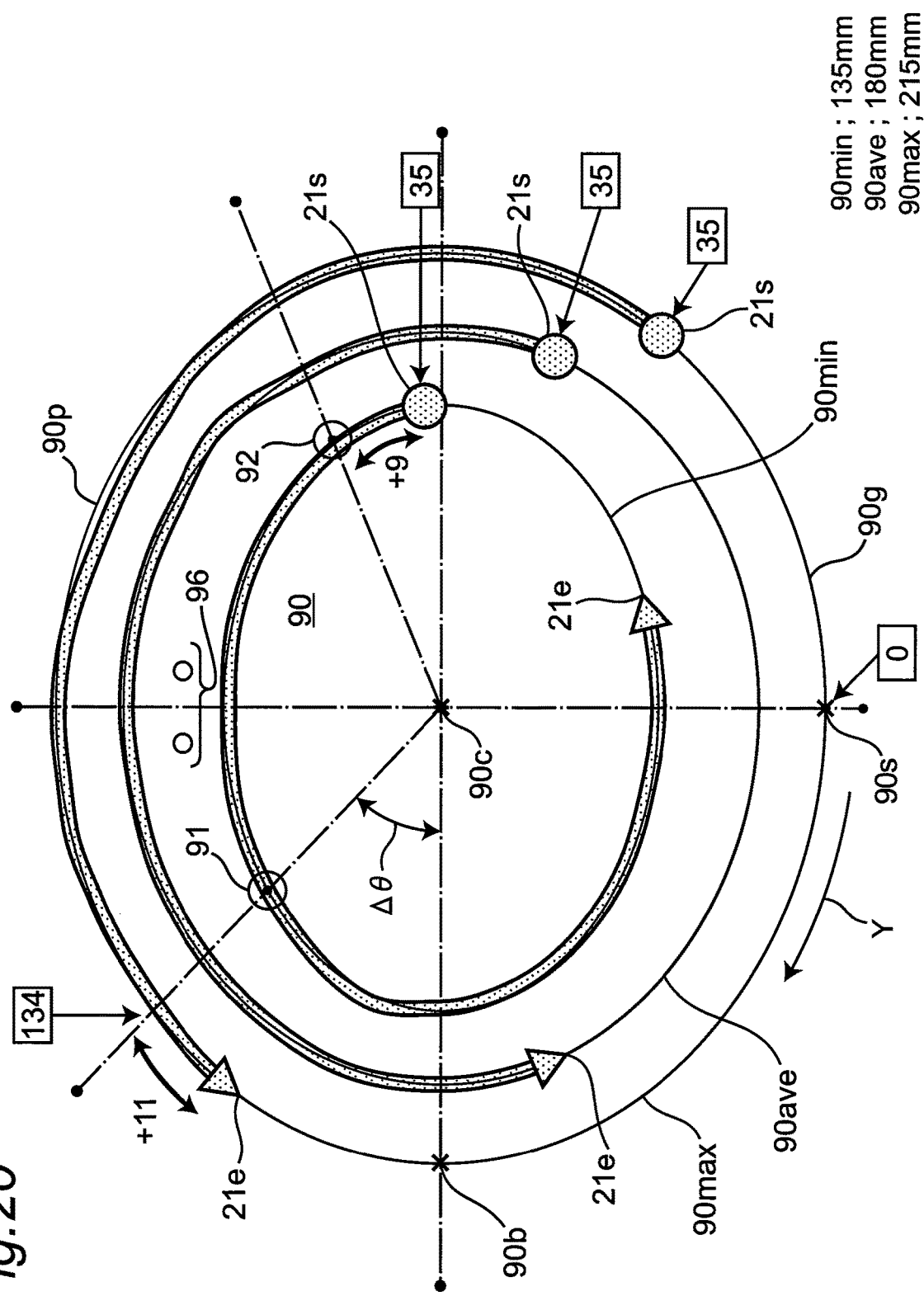
FIG. 20 is a view schematically showing a range occupied by the sensing cuff in a circumferential direction of each wrist having either a maximum wrist circumference, an average wrist circumference, or a minimum wrist circumference.
Figure 21:
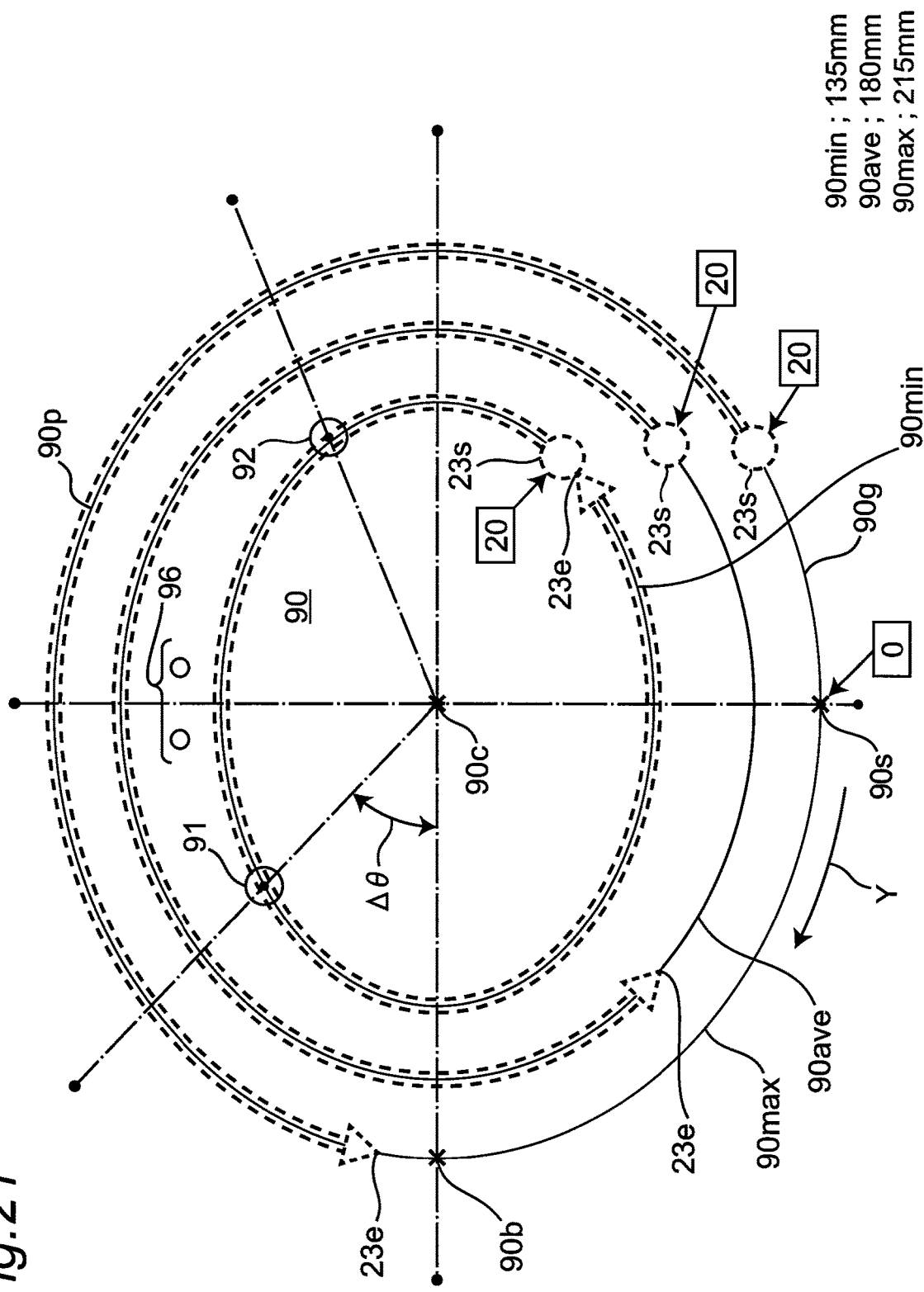
FIG. 21 is a view schematically showing a range occupied by the pressure cuff in a circumferential direction of each wrist having either a maximum wrist circumference, an average wrist circumference, or a minimum wrist circumference.

How to set the lengths of the pressure cuff 23 and the sensing cuff 21 will be specifically described with reference to FIGS. 20 and 21. FIGS. 20 and 21 schematically show a left wrist 90max having a maximum wrist circumference, a left wrist 90ave having an average wrist circumference, and a left wrist 90min having a minimum wrist circumference, each represented by an ellipse. In this example, as the product specifications of the sphygmomanometer 1, the maximum wrist circumference is set to 215 mm, and the minimum wrist circumference is set to 135 mm. Also, the average wrist circumference is set to 180 mm. As described above, the dimension of the pressure cuff 23 in the longitudinal direction Y is set to L2=140 mm, and the dimension of the sensing cuff 21 in the longitudinal direction Y is set to L4=110 mm.

In FIG. 20, the range occupied by the sensing cuff 21 for each of the left wrists 90max, 90ave, and 90min is represented by a solid double arrow. The length of the sensing cuff 21 is set to a length that covers the radial artery 91 beyond the ulnar artery 92 from a point (start point) 21s having a circumferential length of 35 mm close to the ulnar side end portion of the main body 10 counterclockwise (in FIG. 20) along the circumferential direction of the left wrist 90max having the maximum wrist circumference. More specifically, an end point (other end) 21e of the sensing cuff 21 on a side opposite to the start point 21s terminates at a point with a circumferential length of 145 mm within the range Δθ between an angle of the radial artery 91 viewed from the center 90c of the left wrist 90max and an angle of the boundary line 90b on the radial side between the dorsal surface 90g and the palmar surface 90p. That is, 145 mm−35 mm=110 mm=L4. The end point 21e of the sensing cuff 21 exceeds the point of the circumferential length of 134 mm corresponding to the radial artery 91 by 11 mm. This 11 mm is a margin in which the sensing cuff 21 covers the radial artery 91. In the left wrist 90ave having the average wrist circumference, the start point 21s of the sensing cuff 21 gets slightly close to the ulnar artery 92, and the end point 21e of the sensing cuff 21 goes beyond the boundary line 90b on the radial side. In the left wrist 90min having the minimum wrist circumference, the start point 21s of the sensing cuff 21 gets further close to the ulnar artery 92, and the end point 21e of the sensing cuff 21 goes beyond the center 90s of the dorsal surface 90g. However, a margin of 9 mm still remains between the start point 21s of the sensing cuff 21 and the point corresponding to the ulnar artery 92. In addition, the end point 21e of the sensing cuff 21 is sufficiently separated from the start point 21s of the sensing cuff 21.

In FIG. 21, the range occupied by the pressure cuff 23 for each of the left wrists 90max, 90ave, and 90min is represented by a dashed double arrow. The length of the pressure cuff 23 is set to a length that covers the radial artery 91 beyond the ulnar artery 92 from a point (start point) 23s having a circumferential length of 20 mm close to the ulnar side end portion of the main body 10 counterclockwise (in FIG. 21) along the circumferential direction of the left wrist 90max having the maximum wrist circumference. More specifically, the end point (the other end) 23e of the pressure cuff 23 on a side opposite to the start point 23s terminates at a point with a circumferential length of 160 mm within the range Δθ between an angle of the radial artery 91 viewed from the center 90c of the left wrist 90max and an angle of the boundary line 90b on the radial side between the dorsal surface 90g and the palmar surface 90p (Note that the boundary line 90b on the radial side of the left wrist 90max having the maximum wrist circumference corresponds to a circumference length of approximately 161 mm). That is, 160 mm−20 mm=140 mm=L2. In the left wrist 90ave having the average wrist circumference, the start point 23s of the pressure cuff 23 gets slightly close to the ulnar artery 92, and the end point 23e of the pressure cuff 23 goes beyond the boundary line 90b on the radial side. In the left wrist 90min having the minimum wrist circumference, the start point 23s of the pressure cuff 23 gets further close to the ulnar artery 92, and the end point 23e of the pressure cuff 23 goes beyond the center 90s of the dorsal surface 90g and reaches the start point 23s of the pressure cuff 23. However, the overlap between the start point 23s side and the end point 23e side of the pressure cuff 23 occurs only in a slight range.

Figure 22:
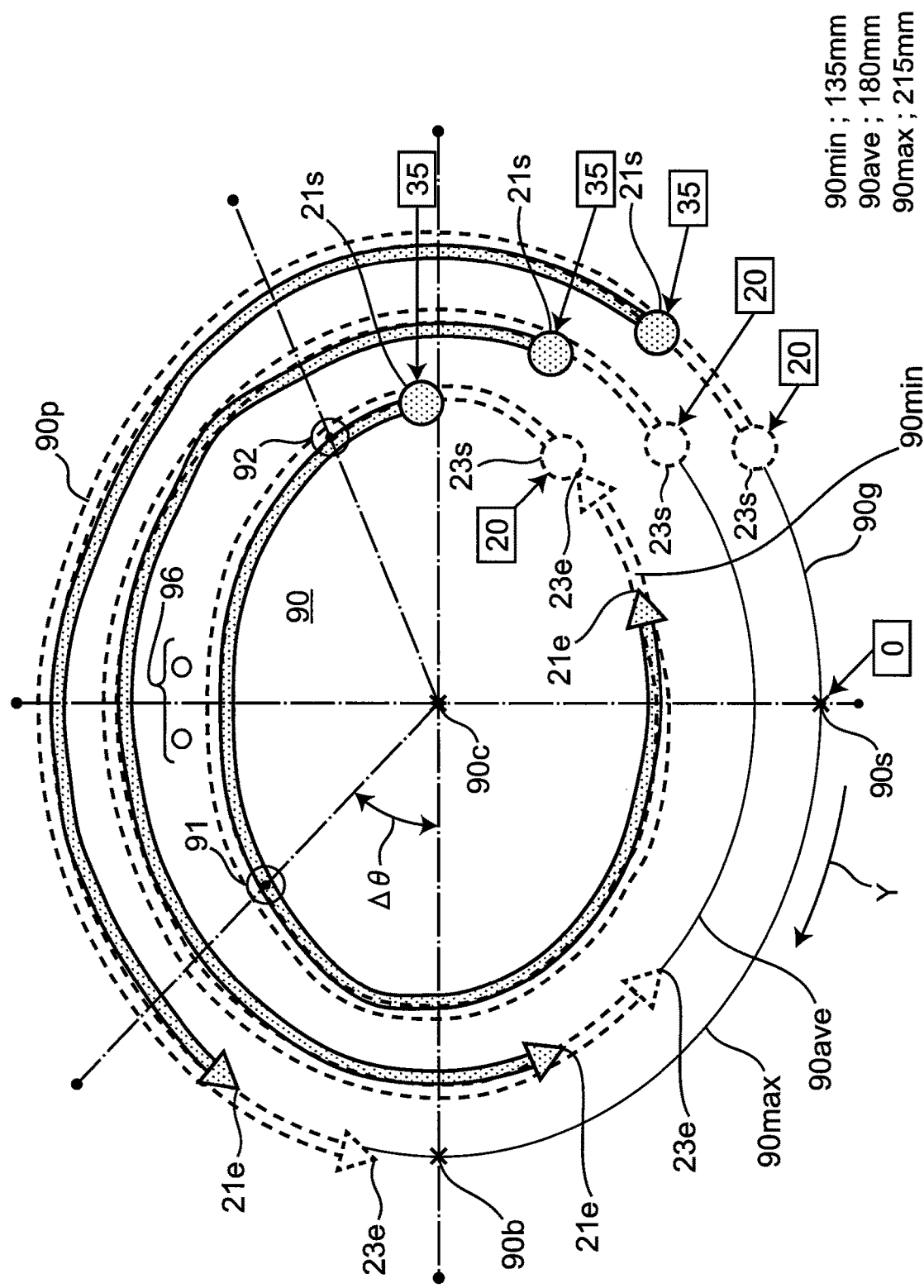
FIG. 22 is a view schematically showing an overlapped range occupied by the sensing cuff and the pressure cuff in a circumferential direction of each wrist having either a maximum wrist circumference, an average wrist circumference, or a minimum wrist circumference.

In FIG. 22, for each of the left wrists 90max, 90ave, and 90min, the range occupied by the sensing cuff 21 shown in FIG. 20 is represented by a solid double arrow, and the range occupied by the pressure cuff 23 shown in FIG. 21 is represented by a dashed double arrow. In any of the cases, the range occupied by the pressure cuff 23 exceeds the range occupied by the sensing cuff 21. Accordingly, the pressure cuff 23 can press the entire area of the sensing cuff 21 in the circumferential direction Y via the back plate 22. Accordingly, the sensing cuff 21 covers both the ulnar artery 92 and the radial artery 91 and can detect a pulse wave of blood flow from both the ulnar artery 92 and the radial artery 91. The lengths of the back plate 22 and the curler 24 may be set in accordance with the lengths of the pressure cuff 23 and the sensing cuff 21.

Figure 23:
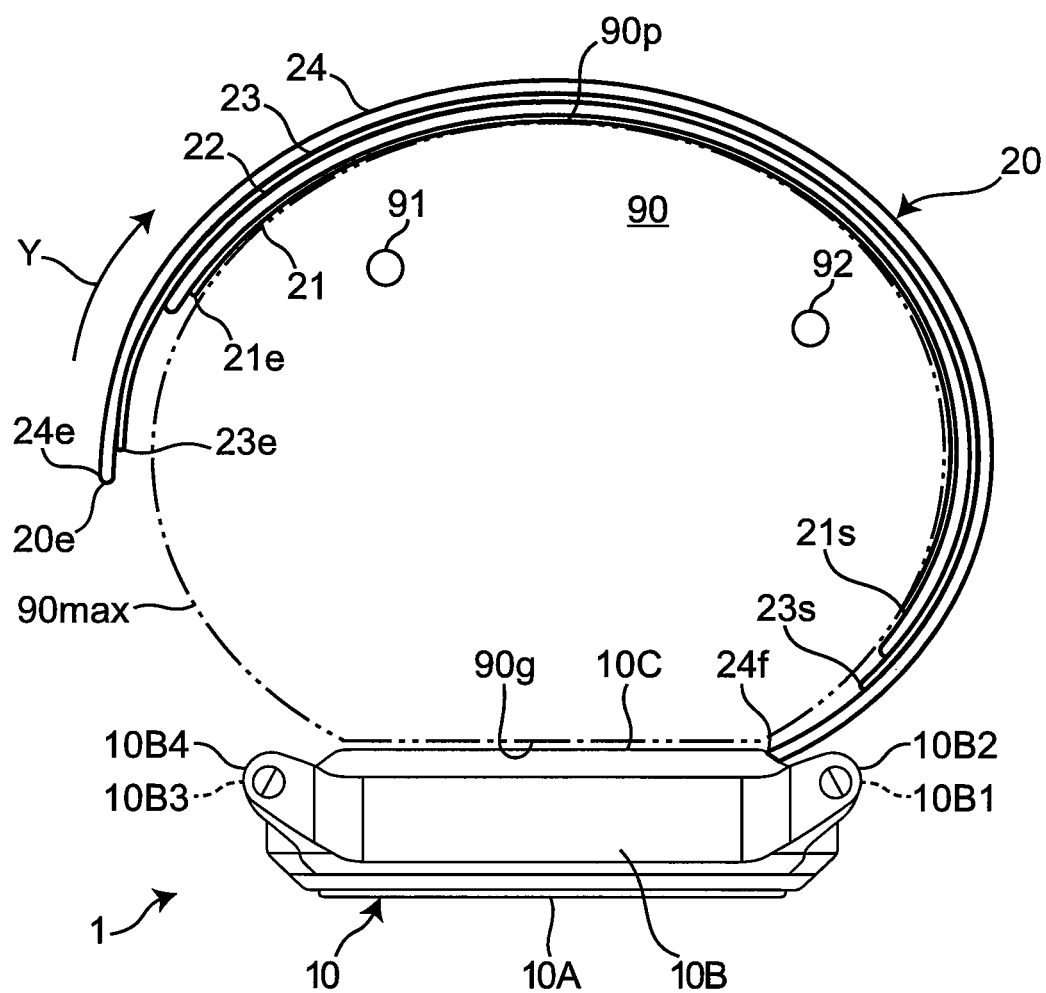
FIG. 23 shows a cross section perpendicular to the left wrist, with the sphygmomanometer attached to the left wrist having a maximum wrist circumference.
Figure 24:
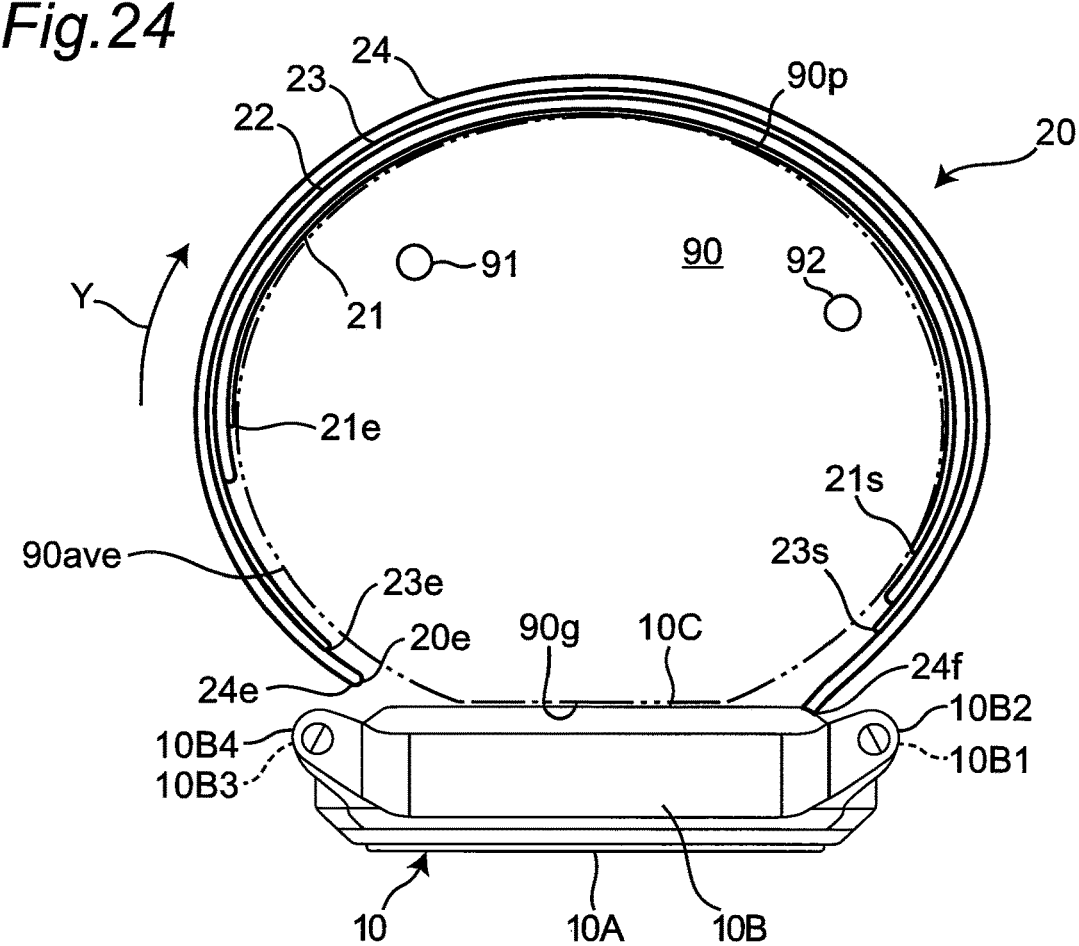
FIG. 24 shows a cross section perpendicular to the left wrist, with the sphygmomanometer attached to the left wrist having an average wrist circumference.
Figure 25:
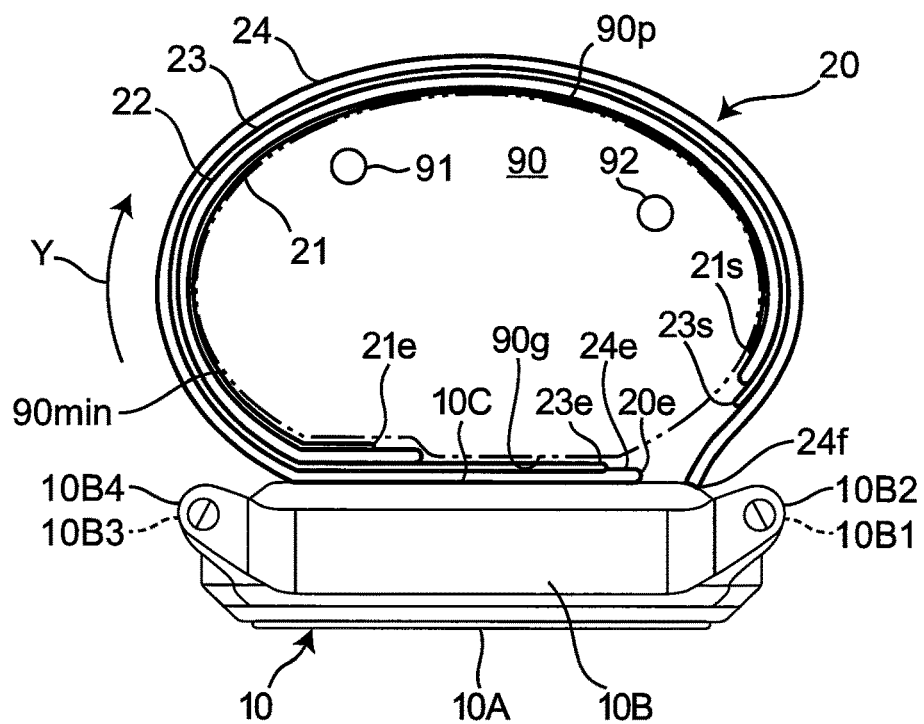
FIG. 25 shows a cross section perpendicular to the left wrist, with the sphygmomanometer attached to the left wrist having a minimum wrist circumference.

FIGS. 23, 24, and 25 show the sphygmomanometer 1 attached to the left wrist 90max having the maximum wrist circumference, the left wrist 90ave having the average wrist circumference, and the left wrist 90min having the minimum wrist circumference. As shown in FIG. 23, in the left wrist 90max having the maximum wrist circumference, although the tip end (other end) 20e (the tip end portion 24e of the curler 24) of the cuff structure 20 is separated from the main body 10, the radial artery 91 is sufficiently covered beyond the ulnar artery 92 by the cuff structure 20 (the sensing cuff 21 in particular). As shown in FIG. 24, in the left wrist 90ave having the average wrist circumference, the tip end 20e of the cuff structure 20 substantially reaches the main body 10. As shown in FIG. 25, in the left wrist 90min having the minimum wrist circumference, the tip end 20e of the cuff structure 20 is clamped between the back lid 10C of the main body 10 and the dorsal surface 90g of the left wrist 90. However, the start point 23s side and the end point 23e side of the pressure cuff 23 are separated from each other and do not overlap. This is because when the sphygmomanometer 1 attached, the cuff structure 20 is slightly bent in the vicinity of the radial side end portion (end portion on the side of the lugs 10B3 and 10B4) of the main body 10, the left wrist 90 is slightly deformed, and the like. This successfully avoids the problem that a portion continuing to the tip end 20e of the cuff structure 20 becomes surplus making difficult to be attached.

As described above, according to the sphygmomanometer 1, even with the left wrist 90max having the maximum wrist circumference, the cuff structure 20 covers both the ulnar artery 92 and the radial artery 91 beyond the ulnar artery 92. Since the cuff structure 20 is disposed extending along the circumferential direction of the wrist from the ulnar side end portion (the end portion on the side of the lugs 10B1 and 10B2) of the main body 10 to the palmar surface 90p, the length of the cuff structure 20 can be kept short as compared with the case in which the cuff structure 20 extends along the circumferential direction of the wrist from the radial side end portion (the end portion on the side of the lugs 10B3 and 10B4) of the main body 10 to the palmar surface 90p. As a result, the sphygmomanometer 1 is easily attached even to a user with a small wrist circumference (minimum wrist circumference in particular). Thus, the sphygmomanometer 1 can be preferably applied to users with wrist circumferences of various sizes.

While in the embodiment described above, the example in which the sensing cuff 21 is in direct contact with the left wrist 90 as the measurement target site has been described, the present invention is not limited thereto. The sensing cuff 21 may come into contact with the left wrist 90 indirectly via another member (cover member for example).

In the embodiment described above, the cuff structure 20 includes the pressure cuff 23 and the sensing cuff 21 separately, but the present invention is not limited thereto. In the present invention, in the cuff structure 20, the portion to which a fluid for pressurization control by the pressurization control unit is supplied and the portion in which a fluid for blood pressure calculation by the blood pressure calculation unit is contained may be in common with each other. In that case, the configuration of the sphygmomanometer can be simplified.

In the embodiment described above, the belt 2 and the cuff structure 20 are provided separately from each other, but the present invention is not limited thereto. The belt 2 and the cuff structure 20 may be configured as an integral cuff. In that case, the configuration of the sphygmomanometer can be further simplified.

In the embodiment described above, the measurement target site to which the sphygmomanometer is mounted is the left wrist 90. However, the present invention is not limited thereto. The sphygmomanometer according to the present invention may be configured to be optically symmetrical with respect to the sphygmomanometer 1 shown in FIGS. 1 and 2 and attached to the right wrist.

In the embodiment described above, the main body 10 and the belt 2 are formed separately from each other, and the belt 2 is attached to the main body 10. However, the present invention is not limited thereto. The main body 10 and the belt 2 may be integrally molded.

In the embodiment described above, the first belt portion 3 and the second belt portion 4 of the belt 2 are fastened or released by the clasp 5. However, the present invention is not limited thereto. For example, the first belt portion 3 and the second belt portion 4 may be coupled to each other via an openable three-fold buckle.

In the embodiment described above, the CPU 100 mounted on the sphygmomanometer 1 serves as a fluid containment control unit, a pressurization control unit, and a blood pressure calculation unit, and executes blood pressure measurement (operation flow in FIG. 11). However, the present invention is not limited thereto. A substantial computer device such as a smartphone provided outside the sphygmomanometer 1, for example, serves as a fluid containment control unit, a pressurization control unit, and a blood pressure calculation unit, and may cause the sphygmomanometer 1 to execute blood pressure measurement (operation flow in FIG. 11) via a network 900.

As described above, a sphygmomanometer of the present disclosure comprises:

a main body that is mounted with a pump and is to be disposed on a dorsal surface of a wrist as a measurement target site; and a cuff that extends along a circumferential direction of the wrist from an ulnar side end portion of the main body to a palmar surface and is to be attached around the wrist, wherein the cuff includes a belt that extends from the main body and is to be attached around the wrist, and a cuff structure that has a band shape and a set length, and that is disposed facing an inner circumferential surface of the belt and has one end attached to an ulnar side end portion of the main body, the sphygmomanometer includes a pressurization control unit that performs control of supplying a fluid from the pump to the cuff structure to press the wrist, and a blood pressure calculation unit that calculates a blood pressure based on a pressure of a fluid contained in the cuff structure; and when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference.

In the present specification, the "dorsal surface" of the wrist refers to a semi-circumferential surface corresponding to the back side of the hand of the outer circumferential surface of the wrist. The "palmar surface" of the wrist refers to a semi-circumferential surface corresponding to the palm side of the hand of the outer circumferential surface of the wrist. The "boundary line on a radial side" refers to a boundary line close to the radius, of the two boundary lines between the dorsal surface and the palmar surface.

The "ulnar side end portion" of the main body refers to an end portion of the main body disposed on a side close to the ulna in the circumferential direction of the wrist. On the other hand, the "radial side end portion" of the main body refers to an end portion of the main body disposed on a side close to the radius in the circumferential direction of the wrist.

Also, the "preset maximum wrist circumference" refers to a length set as the maximum wrist circumference that can be measured by the sphygmomanometer in product specifications of the sphygmomanometer, for example, 215 mm.

Also, when simply referred to as the "wrist", it is a generic term for wrists having various sizes of wrist circumferences.

As for the "belt" that "extends from the main body" in the present specification, the main body and the belt may be integrally molded, or the main body and the belt may be formed separately from each other and the belt may be attached to the main body. Furthermore, as for the belt itself, a first belt portion that extends in one direction from the main body and a second belt portion that extends in the other direction from the main body may be fastened or released by a clasp, or may be coupled by an openable buckle. The "inner circumferential surface" of the belt refers to a surface that is on the inner circumferential side with the belt being attached around the measurement target site. Similarly, the "inner circumferential surface" of the pressure cuff refers to a surface that is on the inner circumferential side with the pressure cuff being attached around the measurement target site.

In the sphygmomanometer according to the present disclosure, a main body that is mounted with a pump is disposed on the dorsal surface of a wrist at the time of attaching. A cuff is disposed extending along the circumferential direction of the wrist from the ulnar side end portion of the main body to the palmar surface. In this attached state, the belt that extends from the main body surrounds the wrist, and the band-shaped cuff structure having one end attached to the ulnar side end portion of the main body is attached to the main body while disposed on the inner circumferential side closer to the wrist than the belt is. Herein, when the cuff structure is attached to a wrist having the maximum wrist circumference, the other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference. Accordingly, even in a wrist having the maximum wrist circumference, the cuff structure covers both the ulnar artery and the radial artery beyond the ulnar artery. Since the cuff structure is disposed extending along the circumferential direction of the wrist from the ulnar side end portion of the main body to the palmar surface, the length of the cuff structure can be kept short as compared with the case in which the cuff structure extends along the circumferential direction of the wrist from the radial side end portion of the main body to the palmar surface. In particular, the cuff structure does not go beyond a boundary line on the radial side between the dorsal surface and the palmar surface in the circumferential direction of the wrist having the maximum wrist circumference, and hence the length of the cuff structure is kept relatively short. Accordingly, the sphygmomanometer is easily attached even to a user with a small wrist circumference. Thus, this sphygmomanometer can be preferably applied to users with wrist circumferences of various sizes.

At the time of blood pressure measurement, the pressurization control unit performs control of supplying a fluid from the pump to the cuff structure to press the wrist. The cuff structure presses both the ulnar artery and the radial artery. The blood pressure calculation unit calculates the blood pressure based on the pressure of the fluid contained in the cuff structure in the pressurization process or the depressurization process of the cuff structure (oscillometric method).

The cuff structure only needs to extend by the set length along the circumferential direction of the wrist from the ulnar side end portion of the main body to the palmar surface. The cuff structure does not need to extend along the circumferential direction of the wrist from the radial side end portion of the main body, for example.

In the cuff structure, a portion to which a fluid for pressurization control by the pressurization control unit is supplied and a portion in which a fluid for blood pressure calculation by the blood pressure calculation unit is contained may be in common with each other or may be separated from each other.

In the sphygmomanometer according to one embodiment, the cuff structure includes
a bag-shaped pressure cuff that extends along the circumferential direction of the wrist so as to receive a supply of pressurization fluid to press the wrist,
a sensing cuff that is configured in a bag shape so as to be capable of containing pressure transmission fluid, is disposed along an inner circumferential surface of the pressure cuff, and extends in the circumferential direction across an artery passing portion of the wrist, and
a back plate that is inserted between the pressure cuff and the sensing cuff, extends along the circumferential direction of the wrist, and transmits a pressing force from the pressure cuff to the sensing cuff;
the pressurization control unit performs control of supplying the pressurization fluid from the pump to the pressure cuff to press the wrist; and
the blood pressure calculation unit calculates a blood pressure based on a pressure of the pressure transmission fluid contained in the sensing cuff.

In addition, the "pressure transmission fluid" may be contained in the sensing cuff at the manufacturing stage of the sphygmomanometer, or may also be contained in the sensing cuff and discharged from the sensing cuff each time the blood pressure is measured.

Also, the "fluid" for pressurization or pressure transmission is typically air, but it may be other gas or liquid.

In the sphygmomanometer according to this embodiment, in the attached state, the bag-shaped pressure cuff included in the cuff structure extends along the circumferential direction of the wrist. In addition, the bag-shaped sensing cuff included in the cuff structure is disposed more on the inner circumferential side than the pressure cuff is and extends in the circumferential direction across an artery passing portion of the wrist. The back plate included in the cuff structure is inserted between the pressure cuff and the sensing cuff and extends along the circumferential direction of the wrist.

At the time of blood pressure measurement, for example, a pressure transmission fluid is contained in the sensing cuff. In that state, the pressurization control unit performs control of supplying the pressurization fluid from the pump mounted on the main body to the pressure cuff to press the wrist. At this time, the back plate transmits the pressing force from the pressure cuff to the sensing cuff. The sensing cuff presses the wrist (including the artery passing portion). The blood pressure calculation unit calculates the blood pressure based on the pressure of the pressure transmission fluid contained in the sensing cuff in the pressurization process or the depressurization process of the pressure cuff (oscillometric method).

Here, in this sphygmomanometer, the sensing cuff detects the pressure itself applied to the wrist at an artery passing portion. Accordingly, the blood pressure can be accurately measured, even if the pressure cuff greatly inflates in the thickness direction when pressurized and press loss occurs as a result of setting the width direction dimension of the cuff (the belt and the cuff structure) to be small (about 25 mm for example). In addition, in the attached state, the sensing cuff extends in the circumferential direction across an artery passing portion of the wrist. Accordingly, when the user actually attaches the sphygmomanometer on the wrist, the sensing cuff will not come off from an artery passing portion of the wrist even if the cuff as well as the main body is displaced to a certain extent in the circumferential direction of the wrist. Accordingly, it is possible to prevent the blood pressure measurement value from varying with respect to the actual blood pressure, and as a result, it is possible to accurately measure the blood pressure.

Since the cuff structure is not attached to the belt, the length of the cuff structure, i.e., the dimension in the longitudinal direction (corresponding to the circumferential direction of the wrist) can be set to the optimum dimension regardless of the belt.

It is desirable that the belt is made of a material that has flexibility in the thickness direction of the belt and exhibits substantially no stretchability in the longitudinal direction of the belt (corresponding to the circumferential direction of the wrist). This allows the belt to be easily wrapped around and restrain the outer circumferential side of the cuff structure at the time of attachment, and to help pressing the wrist at the time of blood pressure measurement.

In the sphygmomanometer according to one embodiment, the sensing cuff comes into contact with the wrist.

In the present specification, "contact" includes not only direct contact but also indirect contact via another member (for example, a cover member).

In the sphygmomanometer according to this embodiment, the sensing cuff comes into contact with the wrist. Accordingly, the blood pressure can be measured more accurately.

In the sphygmomanometer according to one embodiment, other end of the cuff structure on a side opposite to the one end is a free end.

In the sphygmomanometer according to this embodiment, the other end of the cuff structure on a side opposite to the one end is a free end. Therefore, when the user collectively surrounds the wrist and the cuff structure with the belt, the cuff structure receives an inward force from the belt, and the cuff structure can slide or deform so as to exactly follow the outer circumferential surface of the wrist. Accordingly, the user can easily attach the cuff (the belt and the cuff structure) on the wrist. Thus, in the attached state, the cuff structure and the belt are substantially in close contact in this order with the outer circumferential surface of the wrist. As a result, blood pressure can be measured accurately.

In the sphygmomanometer according to one embodiment, when the cuff structure is attached to a wrist having the maximum wrist circumference, other end of the sensing cuff on a side opposite to the one end of the cuff structure terminates within a range between an angle of a radial artery viewed from a center of the wrist and an angle of a boundary line on a radial side between the dorsal surface and the palmar surface, with respect to a circumferential direction of the wrist having the maximum wrist circumference.

In the sphygmomanometer according to this embodiment, when the cuff is attached to a wrist having the maximum wrist circumference, the other end of the sensing cuff terminates within a range between an angle of a radial artery viewed from a center of the wrist and an angle of a boundary line on a radial side between the dorsal surface and the palmar surface, with respect to a circumferential direction of a wrist having the maximum wrist circumference. Accordingly, the sensing cuff covers both the ulnar artery and the radial artery and can detect a pulse wave of blood flow from both the ulnar artery and the radial artery.

In the sphygmomanometer according to one embodiment,
  the back plate extends in a band shape beyond a length of the sensing cuff in the circumferential direction of the wrist; and
  the back plate has a plurality of grooves with V-shaped or U-shaped cross sections that extend in a width direction of the back plate and are parallel to and spaced apart from each other in a longitudinal direction of the back plate so that the back plate can be curved along the circumferential direction of the wrist.

In the sphygmomanometer according to this embodiment, the back plate extends in a band shape beyond the length of the sensing cuff in the circumferential direction of the wrist. Accordingly, the back plate can transmit the pressing force from the pressure cuff to the entire area in the longitudinal direction of the sensing cuff (corresponding to the circumferential direction of the wrist). The back plate has a plurality of grooves with V-shaped or U-shaped cross sections that extend in the width direction of the back plate and are parallel to and spaced apart from each other in the longitudinal direction of the back plate so that the back plate can be curved along the circumferential direction of the wrist. Due to this, the back plate does not obstruct the cuff structure from being bent along the circumferential direction of the wrist when the user collectively surrounds the wrist and the cuff structure with the belt at the time of attaching.

In the sphygmomanometer according to one embodiment, the cuff structure includes, along an outer circumferential surface of the pressure cuff, a curler for keeping a shape of the cuff structure in a natural state curved along the circumferential direction of the wrist.

In the present specification, a "curler" refers to a member that is typically formed of a resin plate having a certain degree of flexibility and hardness and that has a shape curved along the circumferential direction surrounding the wrist in a natural state.

The sphygmomanometer according to this embodiment facilitates attachment on the wrist. That is, at the time of attachment, the user first attaches the cuff structure to the wrist (for example, the left wrist) (a first step of attaching). Here, since the cuff structure is curved along the circumferential direction of the wrist by the curler in a natural state, the user can easily attach the cuff structure on the wrist by fitting the cuff structure on the outer circumferential surface of the wrist using the hand (right hand in this example) on one side of the body, which is opposite to the side of body to which the wrist (left wrist in this example) belongs. With the cuff structure attached to the wrist, the cuff structure holds the wrist even if the user releases the hand (right hand in this example) from the cuff structure, and hence the cuff structure (as well as the belt and the main body) is unlikely to come off from the wrist. Next, the user uses the hand (right hand in this example) to collectively surround the wrist and the cuff structure with the belt (a second step of attaching). Thus, the sphygmomanometer of this embodiment can be easily attached to the wrist.

In the sphygmomanometer according to one embodiment, a basal portion on the main body side of the curler that forms the one end of the cuff structure is clamped between a member provided in the main body and a back lid of the main body, and thus the one end of the cuff structure is attached to the main body.

In the sphygmomanometer according to this embodiment, a basal portion of the curler on the main body side, which forms the one end of the cuff structure, is clamped between a member provided in the main body and a back lid of the main body. Due to this, the one end of the cuff structure is attached to the main body. Accordingly, the one end of the cuff structure is reliably held by the main body. At the time of maintenance service, the cuff structure can be replaced with respect to the main body regardless of the belt by opening the back lid of the main body.

If the main body and the belt are formed separately from each other and the belt is attached to the main body, the belt can be replaced with respect to the main body regardless of the cuff structure at the time of maintenance service.

In the sphygmomanometer according to one embodiment,
  the sensing cuff includes a first sheet on a side in contact with the wrist and a second sheet facing the first sheet, and circumferential portions of the first and second sheets are brought into close contact with each other to form the bag shape; and
  a slack that extends in a longitudinal direction of the sensing cuff in a natural state is provided on the first or second sheet at a location continuing to edge portions on both sides of the sensing cuff in a width direction.

The "slack" of the first or second sheet of the sensing cuff can be formed, for example, when the circumferential portions of the first and second sheets are welded together so as to be brought into close contact.

In the sphygmomanometer according to this embodiment, a slack that extends in the longitudinal direction of the sensing cuff in a natural state is provided on the first or second sheet at a location continuing to the edge portions on both sides of the sensing cuff in the width direction. Accordingly, even if the first and second sheets of the sensing cuff are clamped between the pressure cuff (and the back plate) and the wrist and come into contact with each other when the pressure cuff is pressurized, a gap that extends along the longitudinal direction of the sensing cuff (corresponding to the circumferential direction of the wrist) remains at a location continuing to the edge portions on both sides in the width direction of the sensing cuff due to the slack. As a result, the pressure transmission fluid contained in the sensing cuff can flow along the longitudinal direction of the sensing cuff through the gap. Accordingly, the sensing cuff can successfully transmit the pressure applied to an artery passing portion of the wrist to the blood pressure calculation unit as the pressure of the pressure transmission fluid.

The sphygmomanometer according to one embodiment, comprises a fluid containment control unit that performs control of supplying the pressure transmission fluid from the pump to the sensing cuff and causes the sensing cuff to contain the pressure transmission fluid in an attached state where the belt and the cuff structure as well as the main body are attached to the wrist.

In the sphygmomanometer according to this embodiment, the fluid containment control unit performs control of supplying the pressure transmission fluid from the pump to the sensing cuff and causes the sensing cuff to contain the pressure transmission fluid in the attached state. Accordingly, the pressure transmission fluid can be contained in the sensing cuff each time blood pressure is measured. When the blood pressure measurement is completed, the pressure transmission fluid may be discharged from the sensing cuff.

In the sphygmomanometer according to one embodiment, the main body is mounted with the pressurization control unit, the blood pressure calculation unit, and the fluid containment control unit.

The sphygmomanometer of this embodiment can be configured to be compact and integrated. Accordingly, the usability for the user is good.

In another aspect, a blood pressure measurement method of the present disclosure is a method for measuring a blood pressure of a wrist using a sphygmomanometer, the sphygmomanometer including:
  a main body that is mounted with a pump and is to be disposed on a dorsal surface of a wrist as a measurement target site, and
  a cuff that extends along a circumferential direction of the wrist from an ulnar side end portion of the main body to a palmar surface and is to be attached around the wrist,
  wherein the cuff includes
  a belt that extends from the main body and is to be attached around the wrist, and
  a cuff structure that has a band shape and a set length, and that is disposed facing an inner circumferential surface of the belt and has one end attached to an ulnar side end portion of the main body, and
  when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference, and
  the blood pressure measurement method comprises:
  performing control of supplying a fluid from the pump to the cuff structure to press the wrist; and
  calculating a blood pressure based on a pressure of a fluid contained in the cuff structure.

In the blood pressure measurement method of the present disclosure, the main body mounted with the pump is disposed on the dorsal surface of the wrist when attaching. A cuff is disposed extending along the circumferential direction of the wrist from the ulnar side end portion of the main body to the palmar surface. In this attached state, the belt that extends from the main body surrounds the wrist, and the band-shaped cuff structure having one end attached to the ulnar side end portion of the main body is attached to the main body while disposed on the inner circumferential side closer to the wrist than the belt is. Herein, when the cuff structure is attached to a wrist having a preset maximum wrist circumference, the other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference. Accordingly, even in a wrist having the maximum wrist circumference, the cuff structure covers both the ulnar artery and the radial artery beyond the ulnar artery. Since the cuff structure is disposed extending along the circumferential direction of the wrist from the ulnar side end portion of the main body to the palmar surface, the length of the cuff structure can be kept short as compared with the case in which the cuff structure extends along the circumferential direction of the wrist from the radial side end portion of the main body to the palmar surface. In particular, the cuff structure does not go beyond a boundary line on the radial side between the dorsal surface and the palmar surface in the circumferential direction of the wrist having the maximum wrist circumference, and hence the length of the cuff structure is kept relatively short. Accordingly, the cuff and main body are easily attached even to a user with a small wrist circumference. Thus, this blood pressure measurement method can be preferably applied to users with wrist circumferences of various sizes.

At the time of blood pressure measurement, control of supplying a fluid from the pump to the cuff structure to press the wrist is performed. The cuff structure presses both the ulnar artery and the radial artery. The blood pressure is calculated based on the pressure of the fluid contained in the cuff structure in the pressurization process or the depressurization process of the cuff structure (oscillometric method).

In another aspect, a device of the present disclosure is a device comprising a main body that is mounted with blood pressure measurement elements and is to be disposed on a dorsal surface of a wrist as a measurement target site,
  wherein the blood pressure measurement elements include
  a pump mounted to the main body, and
  a cuff that extends along a circumferential direction of the wrist from an ulnar side end portion of the main body to a palmar surface and is to be attached around the wrist,
  wherein the cuff includes
  a belt that extends from the main body and is to be attached around the wrist, and
  a cuff structure that has a band shape and a set length, and that is disposed facing an inner circumferential surface of the belt and has one end attached to an ulnar side end portion of the main body,
  the device includes
  a pressurization control unit that performs control of supplying a fluid from the pump to the cuff structure to press the wrist, and
  a blood pressure calculation unit that calculates a blood pressure based on a pressure of a fluid contained in the cuff structure; and when the cuff structure is attached to a wrist having a preset maximum wrist circumference, other end of the cuff structure on a side opposite to the one end terminates within a range between an angle of a radial artery viewed from a center of the wrist and an angle of a boundary line on a radial side between the dorsal surface and the palmar surface, with respect to a circumferential direction of the wrist having the maximum wrist circumference.

The "device" of the present disclosure widely includes a device having a blood pressure measurement function, and may be configured as, for example, a wristwatch-type wearable device such as a smart watch.

According to the device of the present disclosure, the blood pressure measurement value can be prevented from varying with respect to the actual blood pressure, and as a result, the blood pressure can be measured accurately.

Since the cuff structure is not attached to the belt, the length of the cuff structure, i.e., the dimension in the longitudinal direction (corresponding to the circumferential direction of the wrist) can be set to the optimum dimension regardless of the belt. That is, even in a wrist having the maximum wrist circumference, the cuff structure covers both the ulnar artery and the radial artery beyond the ulnar artery. In particular, the cuff structure does not go beyond a boundary line on the radial side between the dorsal surface and the palmar surface in the circumferential direction of the wrist having the maximum wrist circumference, and hence the length of the cuff structure is kept relatively short. Accordingly, the cuff and main body are easily attached even to a user with a small wrist circumference. Thus, this device can be preferably applied to users with wrist circumferences of various sizes.

As is apparent from the above, the sphygmomanometer, the blood pressure measurement method, and the device according to the present disclosure can be preferably applied to users with wrist circumferences of various sizes.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer comprising:
a main body that is mounted with a pump and is configured to be disposed on a dorsal surface of a wrist as a measurement target site;
a belt that respectively extends from an ulnar side end portion and a radial side end portion of the main body and is configured to be attached around the wrist;
a cuff structure that has a band shape and a set length extending from a first end to a second end on a side opposite to the first end, the first end of the cuff structure being attached to the ulnar side end portion of the main body such that the cuff structure is configured to extend along a circumferential direction of the wrist from the ulnar side end portion of the main body to a palmar surface of the wrist, wherein
in a state that the sphygmomanometer has been assembled, the cuff structure is disposed facing an inner circumferential surface of the belt and is affixed only to the main body and only at the first end in a separable manner from the inner circumferential surface of the belt;
in a state that the sphygmomanometer has been assembled and before being attached to the wrist as the measurement target site, the cuff structure is entirely separated from and external to the inner circumferential surface of the belt and is movable independently relative to the belt; and
a programmed processor configured to:
perform control of supplying a fluid from the pump to the cuff structure to press the wrist, and
calculate a blood pressure based on a pressure of the fluid contained in the cuff structure, wherein:
in an attached state when the belt and the cuff structure together with the main body are configured to be attached to the wrist, the belt respectively extending from the ulnar side end portion and the radial side end portion of the main body is configured to surround and restrain, in the circumferential direction, an outer circumferential side of the cuff structure extending along the circumferential direction of the wrist collectively with the wrist, such that the cuff structure is configured to be pressed to the wrist,
a length of the belt along the circumferential direction is configured to be set variably depending on wrists having different circumferential lengths from each other, such that, when the length of the belt varies, a range along the inner circumferential surface of the belt occupied by the cuff structure having the set length varies relative to the length of the belt, and
when the cuff structure is configured to be attached to a wrist having a preset maximum wrist circumference in the circumferential direction of the wrist having the maximum wrist circumference, the second end of the cuff structure terminates within a range between a first angle of a radial artery viewed from a center of the wrist having the maximum wrist circumference and a second angle of a boundary line on a radial side between the dorsal surface and the palmar surface of the wrist having the maximum wrist circumference.

2. The sphygmomanometer according to claim 1, wherein:
the cuff structure includes:
a bag-shaped pressure cuff that is configured to extend along the circumferential direction of the wrist as the measurement target site so as to receive a supply of the fluid as a pressurization fluid to press the wrist as the measurement target site,
a sensing cuff that is configured in a bag shape so as to be configured to contain a pressure transmission fluid, is disposed along an inner circumferential surface of the pressure cuff, and is configured to extend in the circumferential direction across an artery passing portion of the wrist as the measurement target site, and
a back plate that is inserted between the pressure cuff and the sensing cuff, the back plate being configured to extend along the circumferential direction of the wrist as the measurement target site so as to transmit a pressing force from the pressure cuff to the sensing cuff, and
the programmed processor is configured to perform control of supplying the fluid as the pressurization fluid from the pump to the pressure cuff to press the wrist as the measurement target site, and the programmed processor is configured to calculate a blood pressure based on a pressure of the pressure transmission fluid contained in the sensing cuff.

3. The sphygmomanometer according to claim 2, wherein the sensing cuff is configured to contact with the wrist as the measurement target site.

4. The sphygmomanometer according to claim 2, wherein when the cuff structure is attached to the wrist having the maximum wrist circumference in the circumferential direction of the wrist having the maximum wrist circumference, an other end of the sensing cuff on the side opposite to the first end of the cuff structure terminates within the range between the first angle and the second angle.

5. The sphygmomanometer according to claim 2, wherein
the back plate is configured to extend in a band shape beyond a length of the sensing cuff in the circumferential direction of the wrist as the measurement target site; and
the back plate has a plurality of grooves with V-shaped or U-shaped cross sections that extend in a width direction of the back plate and are parallel to and spaced apart from each other in a longitudinal direction of the back plate so that the back plate is curved along the circumferential direction of the wrist as the measurement target site.

6. The sphygmomanometer according to claim 2, wherein the cuff structure includes, along an outer circumferential surface of the pressure cuff, a curler configured to keep a shape of the cuff structure in a natural state curved along the circumferential direction of the wrist as the measurement target site.

7. The sphygmomanometer according to claim 6, wherein:
the curler is configured to extend in a band shape from a basal portion located on the main body side to a tip end portion on a side opposite to the basal portion along the circumferential direction of the wrist as the measurement target site, and
the basal portion of the curler is clamped, as the first end of the cuff structure, between an inner case member provided in the main body and a back lid of the main body, and thus the first end of the cuff structure is attached to the main body.

8. The sphygmomanometer according to claim 2, wherein:
the sensing cuff includes a first sheet on a side configured to be in contact with the wrist as the measurement target site and a second sheet facing the first sheet, and circumferential portions of the first and second sheets are welded to each other to form the bag shape; and
a slack that extends in a longitudinal direction of the sensing cuff in a natural state is provided on the first or second sheet at a location continuing to edge portions on both sides of the sensing cuff in a width direction.

9. The sphygmomanometer according to claim 2, wherein the programmed processor is configured to perform control of supplying the fluid as the pressure transmission fluid from the pump to the sensing cuff so as to cause the sensing cuff to contain the fluid as the pressure transmission fluid in the attached state.

10. The sphygmomanometer according to claim 9, wherein the main body is mounted with the programmed processor.

11. The sphygmomanometer according to claim 1, wherein, in the state that the sphygmomanometer has been assembled, the second end of the cuff structure is a free end.

12. The sphygmomanometer according to claim 1, wherein the belt includes:
a first belt portion that extends from the ulnar side end portion of the main body;
a second belt portion that extends from the radial side end portion of the main body; and
a clasp or a buckle that is configured to couple the first belt portion to the second belt portion in a manner such that the length of the belt along the circumferential direction is set variably depending on the wrists having the different circumferential lengths from each other.

13. A blood pressure measurement method for measuring a blood pressure of a wrist using a sphygmomanometer, the sphygmomanometer including:
a main body that is mounted with a pump and is configured to be disposed on a dorsal surface of a wrist as a measurement target site,
a belt that respectively extends from an ulnar side end portion and a radial side end portion of the main body and is configured to be attached around the wrist,
a programmed processor, and
a cuff structure that has a band shape and a set length extending from a first end to a second end on a side opposite to the first end, the first end of the cuff structure being attached to the ulnar side end portion of the main body such that the cuff structure is configured to extend along a circumferential direction of the wrist from the ulnar side end portion of the main body to a palmar surface of the wrist, wherein
in a state that the sphygmomanometer has been assembled, the cuff structure is disposed facing an inner circumferential surface of the belt and is affixed only to the main body and only at the first end in a separable manner from the inner circumferential surface of the belt,
in a state that the sphygmomanometer has been assembled and before being attached to the wrist as the measurement target site, the cuff structure is entirely separated from and external to the inner circumferential surface of the belt and is movable independently relative to the belt, wherein:
in an attached state when the belt and the cuff structure together with the main body are configured to be attached to the wrist, the belt respectively extending from the ulnar side end portion and the radial side end portion of the main body is configured to surround and restrain, in the circumferential direction, an outer circumferential side of the cuff structure extending along the circumferential direction of the wrist collectively with the wrist, such that the cuff structure is configured to be pressed to the wrist,
a length of the belt along the circumferential direction is configured to be set variably depending on wrists having different circumferential lengths from each other, such that, when the length of the belt varies, a range along the inner circumferential surface of the belt occupied by the cuff structure having the set length varies relative to the length of the belt, and
when the cuff structure is configured to be attached to a wrist having a preset maximum wrist circumference in the circumferential direction of the wrist having the maximum wrist circumference, the second end of the cuff structure terminates within a range between a first angle of a radial artery viewed from a center of the wrist having the maximum wrist circumference and a second angle of a boundary line on a radial side between the dorsal surface and the palmar surface of the wrist having the maximum wrist circumference, the blood pressure measurement method comprising, by the programmed processor:
performing control of supplying a fluid from the pump to the cuff structure to press the wrist as the measurement target site; and
calculating a blood pressure based on a pressure of the fluid contained in the cuff structure.

14. A device having a blood pressure measuring function, the device comprising:
a main body that is mounted with blood pressure measurement elements including at least a pump, and is configured to be disposed on a dorsal surface of a wrist as a measurement target site;
a belt that respectively extends from an ulnar side end portion and a radial side end portion of the main body and is configured to be attached around the wrist;
a cuff structure that has a band shape and a set length extending from a first end to a second end on a side opposite to the first end, the first end of the cuff structure being attached to the ulnar side end portion of the main body such that the cuff structure is configured to extend along a circumferential direction of the wrist from the ulnar side end portion of the main body to a palmar surface of the wrist, wherein
in a state that the device has been assembled, the cuff structure is disposed facing an inner circumferential surface of the belt and is affixed only to the main body and only at the first end in a separable manner from the inner circumferential surface of the belt;
in a state that the device has been assembled and before being attached to the wrist as the measurement target site, the cuff structure is entirely separated from and external to the inner circumferential surface of the belt and is movable independently relative to the belt; and
a programmed processor configured to:
perform control of supplying a fluid from the pump to the cuff structure to press the wrist, and
calculate a blood pressure based on a pressure of the fluid contained in the cuff structure, wherein:
in an attached state when the belt and the cuff structure together with the main body are configured to be attached to the wrist, the belt respectively extending from the ulnar side end portion and the radial side end portion of the main body is configured to surround and restrain, in the circumferential direction, an outer circumferential side of the cuff structure extending along the circumferential direction of the wrist collectively with the wrist, such that the cuff structure is configured to be pressed to the wrist,
a length of the belt along the circumferential direction is configured to be set variably depending on wrists having different circumferential lengths from each other, such that, when the length of the belt varies, a range along the inner circumferential surface of the belt occupied by the cuff structure having the set length varies relative to the length of the belt, and
when the cuff structure is configured to be attached to a wrist having a preset maximum wrist circumference in the circumferential direction of the wrist having the maximum wrist circumference, the second end of the cuff structure terminates within a range between a first angle of a radial artery viewed from a center of the wrist having the maximum wrist circumference and a second angle of a boundary line on a radial side between the dorsal surface and the palmar surface of the wrist having the maximum wrist circumference.

15. A sphygmomanometer comprising:
a main body that is mounted with a pump and is configured to be disposed on a dorsal surface of a wrist as a measurement target site;
a belt that extends respectively from an ulnar side end portion and a radial side end portion of the main body and is configured to be attached around the wrist;
a cuff structure that has a band shape and a set length extending from a first end to a second end on a side opposite to the first end, the first end of the cuff structure being attached to the ulnar side end portion of the main body such that the cuff structure is configured to extend along a circumferential direction of the wrist from the ulnar side end portion of the main body to a palmar surface of the wrist, wherein
in a state that the sphygmomanometer has been assembled, the cuff structure is disposed facing an inner circumferential surface of the belt and is affixed only to the main body and only at the first end in a separable manner from the inner circumferential surface of the belt;
in a state that the sphygmomanometer has been assembled and before being attached to the wrist as the measurement target site, the cuff structure is entirely separated from and external to the inner circumferential surface of the belt and is movable independently relative to the belt; and
a programmed processor configured to:
perform control of supplying a fluid from the pump to the cuff structure to press the wrist, and
calculate a blood pressure based on a pressure of the fluid contained in the cuff structure, wherein:
in an attached state when the belt and the cuff structure together with the main body are configured to be attached to the wrist, the belt respectively extending from the ulnar side end portion and the radial side end portion of the main body is configured to surround and restrain, in the circumferential direction, an outer circumferential side of the cuff structure extending along the circumferential direction of the wrist collectively with the wrist, such that the cuff structure is configured to be pressed to the wrist, and
a length of the belt along the circumferential direction is configured to be set variably depending on wrists having different circumferential lengths from each other, such that, when the length of the belt varies, a range along the inner circumferential surface of the belt occupied by the cuff structure having the set length varies relative to the length of the belt.

* * * * *